United States Patent
Surrey et al.

(10) Patent No.: US 8,597,651 B2
(45) Date of Patent: Dec. 3, 2013

(54) MONOMERIC VHH DOMAIN DERIVED FROM ANTI-VP6 CAMELID ANTIBODIES, DIMERIC DOMAIN, IMMUNISATION METHOD, ROTAVIRUS DETECTION METHOD, COMPOSITION, PREVENTION AND TREATMENT METHODS FOR ROTAVIRUS INFECTIONS

(75) Inventors: Thomas Surrey, Heidelberg (DE); Aurelien Olichon, Noé (FR); Lorena Laura Garaicoeachea, Ciudad de Buenos Aires (AR); Gisela Ariana Marcoppido, Ciudad de Buenos Aires (AR); Gladys Viviana Parreño, Ciudad de Buenos Aires (AR); Silvia Gómez Sebastián, Madrid (ES); José Angel Martinez Escribano, Madrid (ES); Andrés Wigdorovitz, Buenos Aires (AR)

(73) Assignee: Instituto Nacional de Tecnologia Agropecuaria (INTA), Buenos Aires (AR)

( * ) Notice: Subject to any disclaimer, the term of this patent is extended or adjusted under 35 U.S.C. 154(b) by 602 days.

(21) Appl. No.: 12/670,409

(22) PCT Filed: Jul. 24, 2008

(86) PCT No.: PCT/EP2008/059745
§ 371 (c)(1),
(2), (4) Date: Jun. 14, 2010

(87) PCT Pub. No.: WO2009/016100
PCT Pub. Date: Feb. 5, 2009

(65) Prior Publication Data
US 2010/0330068 A1 Dec. 30, 2010

(30) Foreign Application Priority Data
Jul. 27, 2007 (AR) ................................. P070103331

(51) Int. Cl.
*A61K 39/42* (2006.01)
*A61K 38/00* (2006.01)
*C07K 16/10* (2006.01)

(52) U.S. Cl.
USPC ....................... 424/159.1; 514/1.1; 530/387.1

(58) Field of Classification Search
None
See application file for complete search history.

(56) References Cited

FOREIGN PATENT DOCUMENTS

WO 2006056306 A2 6/2006

OTHER PUBLICATIONS

Corthesy, Blaise, et al., Rotavirus Anti-VP6 Secretory Immunoglobulin A Contributes to Protection via Intracellular Neutralization but Not via Immune Exclusion, Journal of Virology, 2006, pp. 10692-10699, vol. 80, No. 21.
Pant, Neha, ete al., Lactobacilli Expressing Variable Domain of Llama Heavy-Chain Antibody Fragments (Lactobodies) Confer Protection against Rotavirus-Induced Diarrhea, Journal of Infectious Diseases, 2006, pp. 1580-1588, vol. 194.
Van Der Vaart, J.M., et al., Reduction in morbidity of rotavirus induced diarrhoea in mice by yeast produced monovalent llamaderived antibody fragments, Vaccine, 2006, pp. 4130-4137, vol. 24.
McNeal, Monica M., et al., Protection against rotavirus shedding after intranasal immunization of mice with a chimeric VP6 protein does not require intestinal IgA, Virology, 2006, pp. 338-347, vol. 346.
Garaicoechea, Lorena, et al., Llama-Derived Single-Chain Antibody Fragments Directed to Rotavirus VP6 Protein Possess Broad Neutralizing Activity in Vitro and Confer Protection against Diarrhea in Mice, Journal of Virology, 2008, pp. 9753-9764, vol. 82, No. 19.
European Patent Office, International Search Report, PCT/EP2008/059745, Dec. 12, 2008.

*Primary Examiner* — Nicole Kinsey White
(74) *Attorney, Agent, or Firm* — Tristan A. Fuierer; Andrew D. Gerschutz; Moore & Van Allen, PLLC

(57) ABSTRACT

Monomeric VHH domain derived from anti-VP6 camelid antibodies, dimeric domain, immunization method, rotavirus detection method, vaccine composition, prevention and treatment methods for rotavirus infections, wherein said domain may be any of the amino acid sequences shown in SEQ ID No. 1, SEQ ID No. 2, SEQ ID No. 3 or SEQ ID No. 4, and wherein said domains bind to protein VP6 of Group A rotavirus.

17 Claims, 11 Drawing Sheets

FIG. 3

A
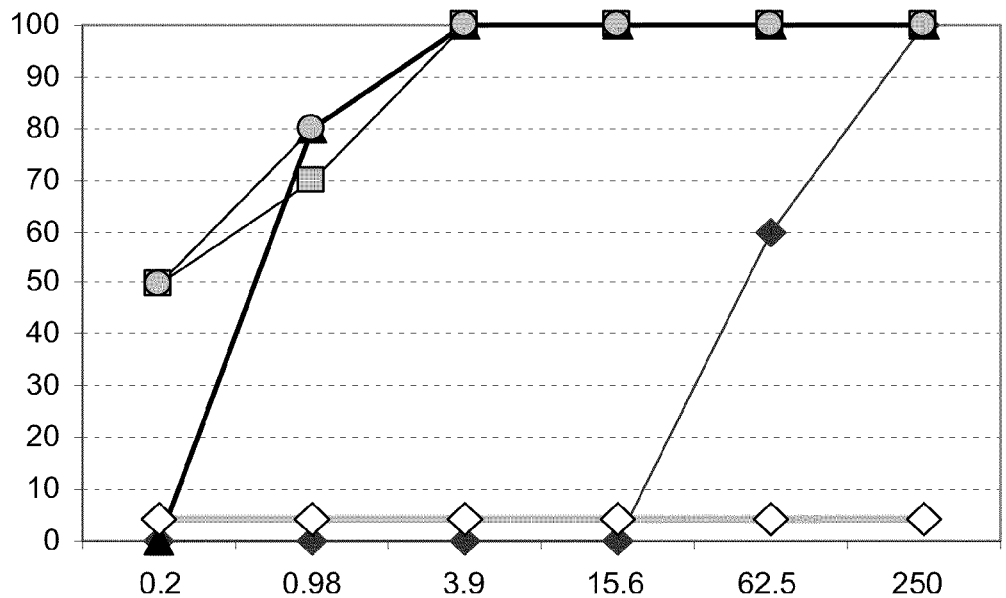
B
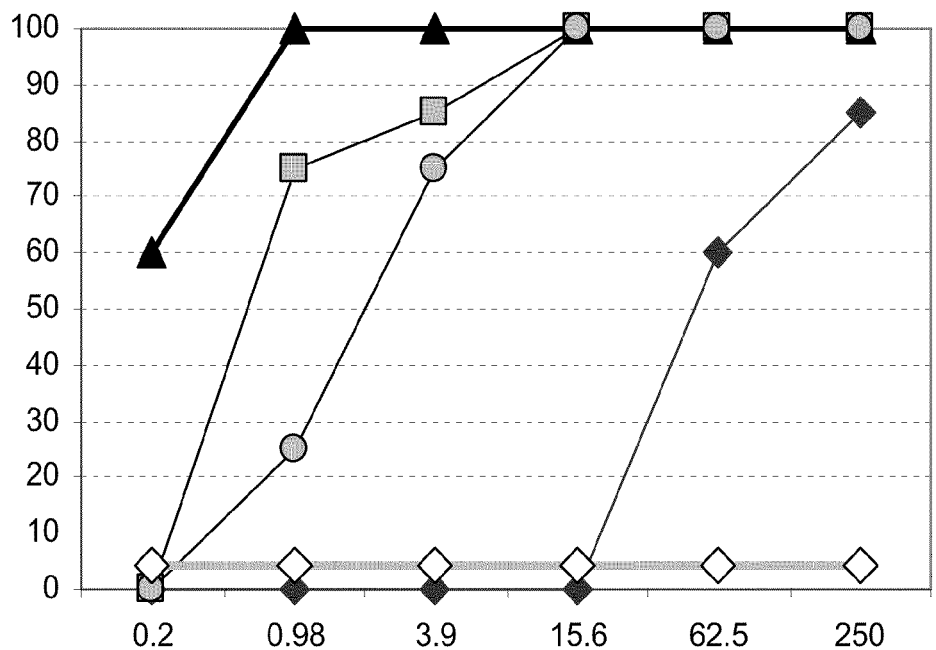
FIG. 4 (A, B)

C
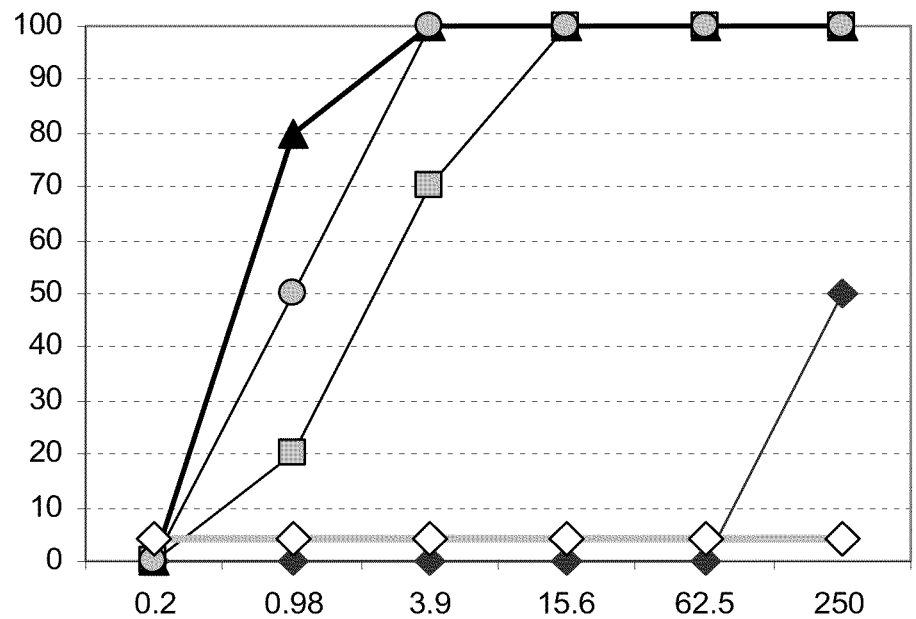
D
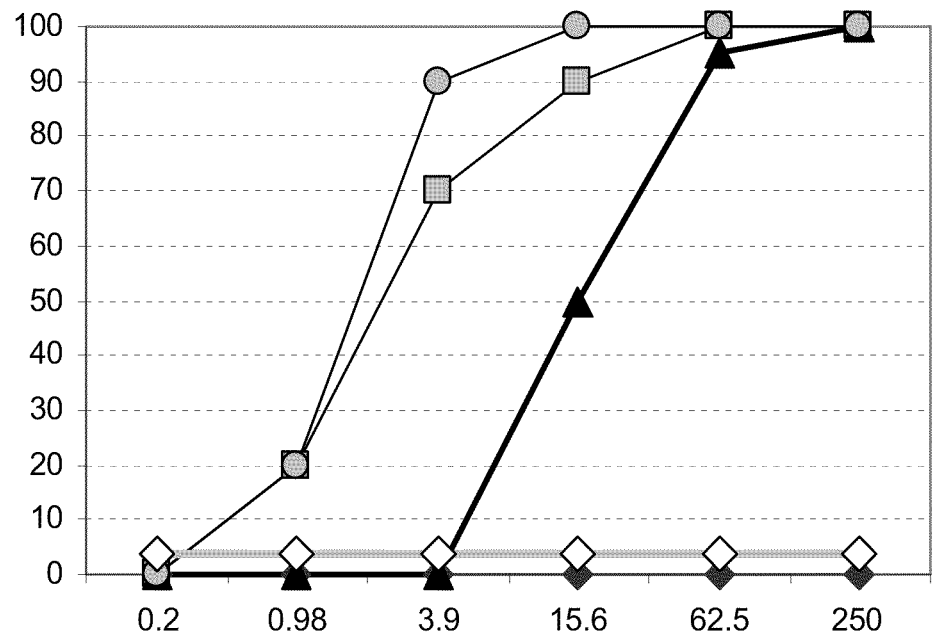
FIG. 4 (C, D)

B
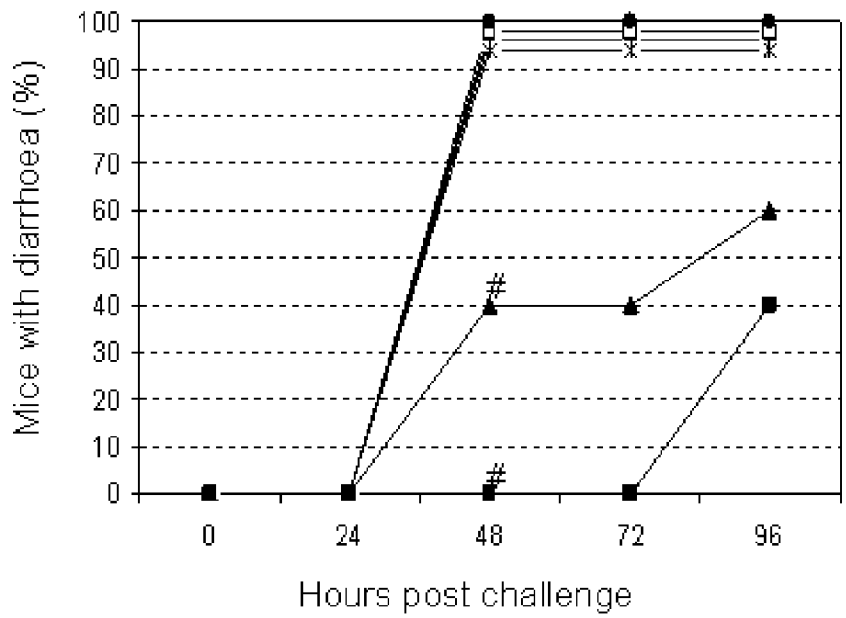
C
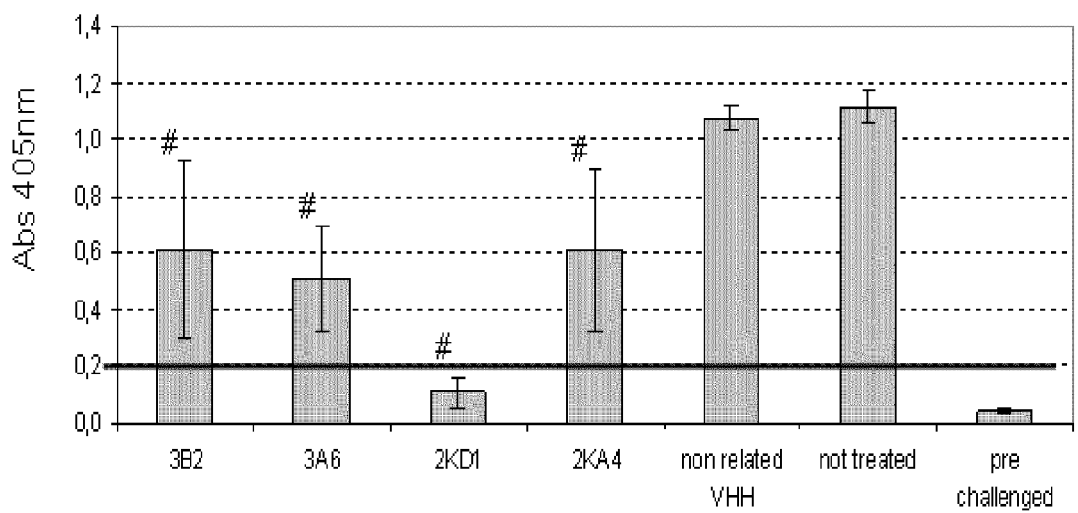
FIG. 5 (B, C)

SEQUENCE LISTING

```
<160> NUMBER OF SEQ ID NOS: 24

<210> SEQ ID NO 1
<211> LENGTH: 129
<212> TYPE: PRT
<213> ORGANISM: Lama glama

<400> SEQUENCE: 1

Met Ala Asp Val Gln Leu Gln Ala Ser Gly Gly Gly Leu Val Gln Ala
1               5                   10                  15

Gly Asp Ser Leu Arg Leu Ser Cys Val Gln Ser Gly Pro Gly Arg Tyr
            20                  25                  30

Gly Val Gly Trp Phe Arg Gln Ala Pro Gly Lys Glu Arg Glu Phe Val
        35                  40                  45

Ala Ala Val Ser Gly Ser Gly Ser Lys Tyr Tyr Gly Asp Ser Val
    50                  55                  60
```

```
Gln Gly Arg Phe Thr Ile Ser Lys Asp Asp Ala Lys Asn Thr Val Tyr
 65                  70                  75                  80

Leu Gln Met Asn Asn Leu Lys Pro Glu Asp Thr Ala Val Tyr Tyr Cys
                 85                  90                  95

Ala Val Arg Arg Thr Tyr Ser Gly Ser Asn Leu Trp His Arg Ser Asp
            100                 105                 110

Glu Tyr Asp Ser Trp Gly Pro Gly Thr Gln Val Thr Val Ser Ser Gly
        115                 120                 125

Arg

<210> SEQ ID NO 2
<211> LENGTH: 126
<212> TYPE: PRT
<213> ORGANISM: Lama glama

<400> SEQUENCE: 2

Met Ala Asp Val Gln Leu Gln Ala Ser Gly Gly Gly Phe Val Gln Pro
  1               5                  10                  15

Gly Asp Ser Leu Ser Leu Ser Cys Ala Ala Ser Gly Gly Thr Phe Ser
                 20                  25                  30

Ser Tyr Ser Ile Gly Trp Phe Arg Gln Gly Pro Gly Lys Glu Arg Glu
             35                  40                  45

Phe Val Ala Thr Ile Ser Ser Asp Ser Pro Trp Tyr Gly Glu Pro
 50                  55                  60

Ala Lys Gly Arg Phe Thr Val Ala Arg Val Asn Ala Lys Asn Thr Ala
 65                  70                  75                  80

Tyr Leu His Leu Asn Arg Leu Lys Pro Glu Asp Thr Ala Thr Tyr Tyr
                 85                  90                  95

Cys Ala Ala Gly Ser Val Gln His Met Ala Asn Glu Asn Glu Tyr Val
            100                 105                 110

Tyr Trp Gly Gln Gly Thr Gln Val Thr Val Ser Ser Gly Arg
        115                 120                 125

<210> SEQ ID NO 3
<211> LENGTH: 127
<212> TYPE: PRT
<213> ORGANISM: Lama glama

<400> SEQUENCE: 3

Met Ala Glu Val Gln Leu Gln Ala Ser Gly Gly Gly Phe Val Gln Pro
  1               5                  10                  15

Gly Gly Ser Leu Ser Leu Ser Cys Ala Val Ser Gly Arg Ser Phe Gly
                 20                  25                  30

Asp Asp Val Met Gly Trp Phe Arg Gln Ala Pro Gly Lys Glu Arg Glu
             35                  40                  45

Phe Val Ser Ala Ile Arg Phe Arg Ser Asn Ser Pro Phe Tyr Gly Asp
 50                  55                  60

Pro Gly Lys Gly Arg Phe Thr Ile Ala Arg Asp Ser Ala Lys Asp Thr
 65                  70                  75                  80

Val Tyr Leu His Met Tyr Arg Leu Arg Pro Asp Asp Thr Ala Val Tyr
                 85                  90                  95

Tyr Cys Ala Val Gly Asp Gly Ala Leu Val Asn Arg Ala Ser Asp Tyr
            100                 105                 110

Thr Tyr Trp Gly Gln Gly Thr Gln Val Thr Val Ser Ser Gly Arg
        115                 120                 125

<210> SEQ ID NO 4
```

<211> LENGTH: 128
<212> TYPE: PRT
<213> ORGANISM: Lama glama

<400> SEQUENCE: 4

```
Met Ala Asp Val Gln Leu Gln Ala Ser Gly Gly Gly Leu Ala Gln Ala
1               5                   10                  15

Gly Asp Ser Leu Thr Leu Ser Cys Ala Ala Ser Gly Arg Thr Phe Ser
            20                  25                  30

Gly Tyr Val Val Gly Trp Phe Arg Gln Ala Pro Gly Ala Glu Arg Glu
        35                  40                  45

Phe Val Gly Ala Ile Arg Trp Ser Glu Asp Ser Thr Trp Tyr Gly Asp
50                  55                  60

Ser Met Lys Gly Arg Ile Leu Ile Ser Arg Asn Asn Ile Lys Asn Thr
65                  70                  75                  80

Val Asn Leu Gln Met Phe Asn Leu Lys Pro Glu Asp Thr Ala Val Tyr
                85                  90                  95

Val Cys Ala Ala Gly Ala Gly Asp Ile Val Thr Thr Glu Thr Ser Tyr
            100                 105                 110

Asn Tyr Trp Gly Arg Gly Thr Gln Val Thr Val Ser Ser Arg Gly Arg
        115                 120                 125
```

<210> SEQ ID NO 5
<211> LENGTH: 411
<212> TYPE: DNA
<213> ORGANISM: Lama glama

<400> SEQUENCE: 5

| | | | | | | |
|---|---|---|---|---|---|---|
| atggctgatg | tgcagctgca | ggcgtctggg | ggaggattgg | tgcaggctgg | ggactctctg | 60 |
| agactctcct | gtgtacaatc | tggaccgggc | aggtatggcg | tgggctggtt | ccgccaggct | 120 |
| ccagggaaag | agcgtgaatt | tgtgggcagct | gtgagcggga | gtggtggttc | gaaatattat | 180 |
| ggagactccg | tacagggccg | attcaccatc | tccaaagacg | acgccaagaa | cacggtgtat | 240 |
| ctgcaaatga | acaacctgaa | acctgaggac | acggccgttt | attactgtgc | agtccggaga | 300 |
| acctatagtg | gtagtaacct | ttggcacaga | tcggatgagt | atgactcctg | gggcccgggg | 360 |
| acccaggtca | ccgtctccag | cggccgccac | caccatcacc | atcactaata | g | 411 |

<210> SEQ ID NO 6
<211> LENGTH: 402
<212> TYPE: DNA
<213> ORGANISM: Lama glama

<400> SEQUENCE: 6

| | | | | | | |
|---|---|---|---|---|---|---|
| atggctgatg | tgcagctgca | ggcgtctggg | ggaggatttg | tgcagcctgg | agattctctg | 60 |
| agtctctcct | gtgcagcctc | tggaggcacc | tttagtagct | attccattgg | ctggttccgc | 120 |
| cagggtccag | gaaggagcg | tgagttcgtg | gctactatca | gttcgagtga | tagtccgtgg | 180 |
| tatggagagc | cgcgaaggg | ccgattcacc | gtcgccagag | ttaacgccaa | gaatacggcg | 240 |
| tatctgcact | tgaacaggtt | gaaacctgag | gacacggcca | cttattattg | tgcagccggt | 300 |
| agtgtacaac | acatggcgaa | tgagaatgag | tatgtctatt | ggggccaggg | gacccaggtc | 360 |
| accgtctcca | gcggccgcca | ccaccatcac | catcactaat | ag | | 402 |

<210> SEQ ID NO 7
<211> LENGTH: 405
<212> TYPE: DNA
<213> ORGANISM: Lama glama

<400> SEQUENCE: 7

```
atggctgagg tccagctgca ggcgtctggg ggaggatttg ttcaacctgg gggctctctg      60
agtctctcct gtgccgtctc tggacgcagc ttcggtgacg atgtcatggg ctggttccgc     120
caggctccag ggaaggagcg tgaatttgta tcagctatta ggttcaggag taacagccca     180
ttttatggcg accccgggaa gggccgattc accatcgcca gagacagcgc caaggacacg     240
gtgtatctgc acatgtaccg cctgagacct gacgacacgg ccgtatatta ctgtgccgta     300
ggagatggtg cccttgtgaa tcgcgcgtcc gactatacgt actggggcca ggggacccag     360
gtcaccgtct ccagcggccg ccaccaccat caccatcact aatag                     405
```

<210> SEQ ID NO 8
<211> LENGTH: 408
<212> TYPE: DNA
<213> ORGANISM: Lama glama

<400> SEQUENCE: 8

```
atggctgatg tgcagctgca ggcgtctggg ggaggtttgg cgcaggctgg ggactctctg      60
acactctcct gtgcagcctc tggacgcacc ttcagtggtt atgtcgtggg ctggttccgc     120
caggctccag gggcggagcg tgagtttgta ggagctatta gatggtcaga agatagcaca     180
tggtatggag actccatgaa gggccgaatt ctcatctcca gaacaatat caagaacacg     240
gtgaatctgc aaatgttcaa tctaaaacct gaagacacgg ccgtgtacgt ctgtgcagca     300
ggggccgggg atatagtgac tactgagact tcttataatt actggggccg ggggacccag     360
gtcaccgtct cctcacgcgg ccgccaccac catcaccatc actaatag                  408
```

<210> SEQ ID NO 9
<211> LENGTH: 266
<212> TYPE: PRT
<213> ORGANISM: Lama glama

<400> SEQUENCE: 9

```
Met Ala Asp Val Gln Leu Gln Ala Ser Gly Gly Gly Phe Val Gln Pro
  1               5                  10                  15

Gly Gly Ser Leu Ser Leu Ser Cys Ala Val Ser Gly Arg Ser Phe Gly
             20                  25                  30

Asp Asp Val Met Gly Trp Phe Arg Gln Ala Pro Gly Lys Glu Arg Glu
         35                  40                  45

Phe Val Ser Ala Ile Arg Phe Arg Ser Asn Ser Pro Phe Tyr Gly Asp
     50                  55                  60

Pro Gly Lys Gly Arg Phe Thr Ile Ala Arg Asp Ser Ala Lys Asp Thr
 65                  70                  75                  80

Val Tyr Leu His Met Tyr Arg Leu Arg Pro Asp Asp Thr Ala Val Tyr
                 85                  90                  95

Tyr Cys Ala Val Gly Asp Gly Ala Leu Val Asn Arg Ala Ser Asp Tyr
            100                 105                 110

Thr Tyr Trp Gly Gln Gly Thr Gln Val Thr Val Ser Ser Gly Pro
        115                 120                 125

Ser Thr Pro Pro Arg Pro Ser Pro Ser Thr Pro Ser Asp Val Gln
130                 135                 140

Leu Gln Ala Ser Gly Gly Gly Phe Val Gln Pro Gly Gly Ser Leu Ser
145                 150                 155                 160

Leu Ser Cys Ala Val Ser Gly Arg Ser Phe Gly Asp Asp Val Met Gly
                165                 170                 175

Trp Phe Arg Gln Ala Pro Gly Lys Glu Arg Glu Phe Val Ser Ala Ile
```

```
                    180                 185                 190
Arg Phe Arg Ser Asn Ser Pro Phe Tyr Gly Asp Pro Gly Lys Gly Arg
                195                 200                 205

Phe Thr Ile Ala Arg Asp Ser Ala Lys Asp Thr Val Tyr Leu His Met
            210                 215                 220

Tyr Arg Leu Arg Pro Asp Asp Thr Ala Val Tyr Tyr Cys Ala Val Gly
225                 230                 235                 240

Asp Gly Ala Leu Val Asn Arg Ala Ser Asp Tyr Thr Tyr Trp Gly Gln
                245                 250                 255

Gly Thr Gln Val Thr Val Ser Ser Gly Arg
            260                 265

<210> SEQ ID NO 10
<211> LENGTH: 264
<212> TYPE: PRT
<213> ORGANISM: Lama glama

<400> SEQUENCE: 10

Met Ala Asp Val Gln Leu Gln Ala Ser Gly Gly Gly Phe Val Gln Pro
1               5                   10                  15

Gly Asp Ser Leu Ser Leu Ser Cys Ala Ala Ser Gly Gly Thr Phe Ser
                20                  25                  30

Ser Tyr Ser Ile Gly Trp Phe Arg Gln Gly Pro Gly Lys Glu Arg Glu
            35                  40                  45

Phe Val Ala Thr Ile Ser Ser Asp Ser Pro Trp Tyr Gly Glu Pro
        50                  55                  60

Ala Lys Gly Arg Phe Thr Val Ala Arg Val Asn Ala Lys Asn Thr Ala
65                  70                  75                  80

Tyr Leu His Leu Asn Arg Leu Lys Pro Glu Asp Thr Ala Thr Tyr Tyr
                85                  90                  95

Cys Ala Ala Gly Ser Val Gln His Met Ala Asn Glu Asn Glu Tyr Val
            100                 105                 110

Tyr Trp Gly Gln Gly Thr Gln Val Thr Val Ser Ser Gly Pro Ser
        115                 120                 125

Thr Pro Pro Arg Pro Ser Pro Ser Thr Pro Pro Ser Asp Val Gln Leu
130                 135                 140

Gln Ala Ser Gly Gly Gly Phe Val Gln Pro Gly Asp Ser Leu Ser Leu
145                 150                 155                 160

Ser Cys Ala Ala Ser Gly Gly Thr Phe Ser Ser Tyr Ser Ile Gly Trp
                165                 170                 175

Phe Arg Gln Gly Pro Gly Lys Glu Arg Glu Phe Val Ala Thr Ile Ser
            180                 185                 190

Ser Ser Asp Ser Pro Trp Tyr Gly Glu Pro Ala Lys Gly Arg Phe Thr
        195                 200                 205

Val Ala Arg Val Asn Ala Lys Asn Thr Ala Tyr Leu His Leu Asn Arg
    210                 215                 220

Leu Lys Pro Glu Asp Thr Ala Thr Tyr Tyr Cys Ala Ala Gly Ser Val
225                 230                 235                 240

Gln His Met Ala Asn Glu Asn Glu Tyr Val Tyr Trp Gly Gln Gly Thr
                245                 250                 255

Gln Val Thr Val Ser Ser Gly Arg
            260

<210> SEQ ID NO 11
<211> LENGTH: 267
<212> TYPE: PRT
```

<213> ORGANISM: Lama glama

<400> SEQUENCE: 11

Met Ala Asp Val Gln Leu Gln Ala Ser Gly Gly Leu Ala Gln Ala
1               5                   10                  15

Gly Asp Ser Leu Thr Leu Ser Cys Ala Ala Ser Gly Arg Thr Phe Ser
            20                  25                  30

Gly Tyr Val Val Gly Trp Phe Arg Gln Ala Pro Gly Ala Glu Arg Glu
        35                  40                  45

Phe Val Gly Ala Ile Arg Trp Ser Glu Asp Ser Thr Trp Tyr Gly Asp
    50                  55                  60

Ser Met Lys Gly Arg Ile Leu Ile Ser Arg Asn Asn Ile Lys Asn Thr
65                  70                  75                  80

Val Asn Leu Gln Met Phe Asn Leu Lys Pro Glu Asp Thr Ala Val Tyr
                85                  90                  95

Val Cys Ala Ala Gly Ala Gly Asp Ile Val Thr Thr Glu Thr Ser Tyr
            100                 105                 110

Asn Tyr Trp Gly Arg Gly Thr Gln Val Thr Val Ser Ser Gly Pro
        115                 120                 125

Ser Thr Pro Pro Arg Pro Ser Pro Thr Pro Ser Asp Val Gln
        130                 135                 140

Leu Gln Ala Ser Gly Gly Gly Leu Ala Gln Ala Gly Asp Ser Leu Thr
145                 150                 155                 160

Leu Ser Cys Ala Ala Ser Gly Arg Thr Phe Ser Gly Tyr Val Val Gly
            165                 170                 175

Trp Phe Arg Gln Ala Pro Gly Ala Glu Arg Glu Phe Val Gly Ala Ile
        180                 185                 190

Arg Trp Ser Glu Asp Ser Thr Trp Tyr Gly Asp Ser Met Lys Gly Arg
    195                 200                 205

Ile Leu Ile Ser Arg Asn Asn Ile Lys Asn Thr Val Asn Leu Gln Met
    210                 215                 220

Phe Asn Leu Lys Pro Glu Asp Thr Ala Val Tyr Val Cys Ala Ala Gly
225                 230                 235                 240

Ala Gly Asp Ile Val Thr Thr Glu Thr Ser Tyr Asn Tyr Trp Gly Arg
                245                 250                 255

Gly Thr Gln Val Thr Val Ser Ser Arg Gly Arg
            260                 265

<210> SEQ ID NO 12
<211> LENGTH: 270
<212> TYPE: PRT
<213> ORGANISM: Lama glama

<400> SEQUENCE: 12

Met Ala Asp Val Gln Leu Gln Ala Ser Gly Gly Gly Leu Val Gln Ala
1               5                   10                  15

Gly Ser Asp Ser Leu Arg Leu Ser Cys Val Gln Ser Gly Pro Gly Arg Tyr
            20                  25                  30

Gly Val Gly Trp Phe Arg Gln Ala Pro Gly Lys Glu Arg Glu Phe Val
        35                  40                  45

Ala Ala Val Ser Gly Ser Gly Gly Ser Lys Tyr Tyr Gly Asp Ser Val
    50                  55                  60

Gln Gly Arg Phe Thr Ile Ser Lys Asp Asp Ala Lys Asn Thr Val Tyr
65                  70                  75                  80

Leu Gln Met Asn Asn Leu Lys Pro Glu Asp Thr Ala Val Tyr Tyr Cys
                85                  90                  95

```
Ala Val Arg Arg Thr Tyr Ser Gly Ser Asn Leu Trp His Arg Ser Asp
            100                 105                 110

Glu Tyr Asp Ser Trp Gly Pro Gly Thr Gln Val Thr Val Ser Ser Ser
        115                 120                 125

Gly Pro Ser Thr Pro Pro Arg Pro Ser Pro Ser Thr Pro Pro Ser Asp
    130                 135                 140

Val Gln Leu Gln Ala Ser Gly Gly Leu Val Gln Ala Gly Asp Ser
145                 150                 155                 160

Leu Arg Leu Ser Cys Val Gln Ser Gly Pro Gly Arg Tyr Gly Val Gly
                165                 170                 175

Trp Phe Arg Gln Ala Pro Gly Lys Glu Arg Glu Phe Val Ala Ala Val
            180                 185                 190

Ser Gly Ser Gly Gly Ser Lys Tyr Tyr Gly Asp Ser Val Gln Gly Arg
        195                 200                 205

Phe Thr Ile Ser Lys Asp Asp Ala Lys Asn Thr Val Tyr Leu Gln Met
    210                 215                 220

Asn Asn Leu Lys Pro Glu Asp Thr Ala Val Tyr Tyr Cys Ala Val Arg
225                 230                 235                 240

Arg Thr Tyr Ser Gly Ser Asn Leu Trp His Arg Ser Asp Glu Tyr Asp
                245                 250                 255

Ser Trp Gly Pro Gly Thr Gln Val Thr Val Ser Ser Gly Arg
            260                 265                 270

<210> SEQ ID NO 13
<211> LENGTH: 16
<212> TYPE: PRT
<213> ORGANISM: Homo sapiens

<400> SEQUENCE: 13

Ser Gly Pro Ser Thr Pro Pro Arg Pro Ser Pro Ser Thr Pro Pro Ser
1               5                   10                  15

<210> SEQ ID NO 14
<211> LENGTH: 23
<212> TYPE: DNA
<213> ORGANISM: Artificial Sequence
<220> FEATURE:
<223> OTHER INFORMATION: VHH amplification primer

<400> SEQUENCE: 14
gtcctggctg ctcttctaca agg                                          23

<210> SEQ ID NO 15
<211> LENGTH: 23
<212> TYPE: DNA
<213> ORGANISM: Artificial Sequence
<220> FEATURE:
<223> OTHER INFORMATION: primer to amplify VHH

<400> SEQUENCE: 15
ggtacgtgct gttgaactgt tcc                                          23

<210> SEQ ID NO 16
<211> LENGTH: 65
<212> TYPE: DNA
<213> ORGANISM: Artificial Sequence
<220> FEATURE:
<223> OTHER INFORMATION: primer to amplify VHH

<400> SEQUENCE: 16
aacatgccat gactcgcggc tcaaccggcc atggctgakg tbcagctgca ggcgtctggr    60
``` ggagg 65

<210> SEQ ID NO 17
<211> LENGTH: 53
<212> TYPE: DNA
<213> ORGANISM: Artificial Sequence
<220> FEATURE:
<223> OTHER INFORMATION: primer to amplify VHH

<400> SEQUENCE: 17
attattattc agattattag tgcggccgcg tgaggagacg gtgaccwggg tcc        53

<210> SEQ ID NO 18
<211> LENGTH: 33
<212> TYPE: DNA
<213> ORGANISM: Artificial Sequence
<220> FEATURE:
<223> OTHER INFORMATION: primer to incorporate restriction sites

<400> SEQUENCE: 18
ggctgakgtb cagctgcagg cgtctggrgg agg        33

<210> SEQ ID NO 19
<211> LENGTH: 51
<212> TYPE: DNA
<213> ORGANISM: Artificial Sequence
<220> FEATURE:
<223> OTHER INFORMATION: primer to incorporate restriction sites

<400> SEQUENCE: 19
gttattatta ttcagattat tagtgcggcc gctggagagt gaccwgggtc c        51

<210> SEQ ID NO 20
<211> LENGTH: 48
<212> TYPE: DNA
<213> ORGANISM: Artificial Sequence
<220> FEATURE:
<223> OTHER INFORMATION: primer to amplify dimer sequences

<400> SEQUENCE: 20
ctcgcggccc agccggccat ggcggatgtg cagcttcagg cgtctggg        48

<210> SEQ ID NO 21
<211> LENGTH: 46
<212> TYPE: DNA
<213> ORGANISM: Artificial Sequence
<220> FEATURE:
<223> OTHER INFORMATION: primer to amplify dimer sequences

<400> SEQUENCE: 21
gcattggttc tgcagttgca catctgacgg cggggtggac ggagac        46

<210> SEQ ID NO 22
<211> LENGTH: 43
<212> TYPE: DNA
<213> ORGANISM: Homo sapiens

<400> SEQUENCE: 22
gccgcggcgg ggtagacggg cccgatgagg agacggtgac ctg        43

<210> SEQ ID NO 23
<211> LENGTH: 30
<212> TYPE: DNA
<213> ORGANISM: Artificial Sequence
<220> FEATURE:
<223> OTHER INFORMATION: primer to amplify VHH 3B2 protein

```
<400> SEQUENCE: 23
gcttggatcc tatggctgat gtgcagctgc                                              30

<210> SEQ ID NO 24
<211> LENGTH: 29
<212> TYPE: DNA
<213> ORGANISM: Artificial Sequence
<220> FEATURE:
<223> OTHER INFORMATION: primer to amplify VHH3B2 protein

<400> SEQUENCE: 24
cgtatctaga gcggccgcgt gaggagacg                                               29
```

MONOMERIC VHH DOMAIN DERIVED FROM ANTI-VP6 CAMELID ANTIBODIES, DIMERIC DOMAIN, IMMUNISATION METHOD, ROTAVIRUS DETECTION METHOD, COMPOSITION, PREVENTION AND TREATMENT METHODS FOR ROTAVIRUS INFECTIONS

CROSS-REFERENCE TO RELATED APPLICATIONS

This application is filed under the provisions of 35 U.S.C. §371 and claims the priority of International Patent Application No. PCT/EP2008/059745 filed on 24 Jul. 2008 entitled "Monomeric VHH Domain Derived From ANTI-VP6 Camelid Antibodies, Dimeric Domain, Immunisation Method, Rotavirus Detection Method, Composition, Prevention and Treatment Methods for Rotavirus Infections" in the name of Thomas Surrey, et al., which claims priority of Argentinian Patent Application No. P070103331 filed on 27 Jul. 2007, both of which are hereby incorporated by reference herein in their entirety.

This invention relates to a monomeric VHH domain derived from anti-VP6 camelid antibodies, dimeric domain, immunisation method, rotavirus detection method, compositions, prevention and treatment methods for rotavirus infections. More specifically, it relates to a monomeric domain (VHH) derived from camelid antibodies, where said domain may be any of the amino acid sequences shown in SEQ ID No. 1, SEQ ID No. 2, SEQ ID No. 3 or SEQ ID No. 4, and where said domains bind to protein VP6 of Group A rotavirus.

BACKGROUND OF THE INVENTION

Group A rotavirus (RV) is the main cause of severe diarrhoea in children and in the young of many animal species of economic interest (bovines, porcines, equines, South American camelids, etc.). As a public health problem, RV is the third most common cause of death associated with severe diarrhoea in developing countries (2 million deaths per year). On the other hand, RV-induced diarrhoea in animals intended for consumption, for example young calves, causes high costs related to prevention or treatment.

Group A RV are particles composed of a triple protein capsid. The outer capsid surface is composed of proteins VP4 and VP7, both of which are highly variable antigens; thus far, at least 27 variants of VP4 (P-types) and 16 variants of VP7 (G-types) have been described. Each G-P type combination induces neutralising antibodies that have low cross-reactivity with other G-P types; for this reason, it is necessary to include the different strains that circulate in the target species in the vaccines.

The intermediate capsid is composed of trimeric protein VP6, which represents 51% of the virion mass. Depending on the presence or absence of two different epitopes in protein VP6 (recognised by monoclonal antibodies mAb 255/60 and 631/9), Group A RV strains are additionally classified as subgroups (Sb) I, II, I+II and noI noII. Human RV are usually Sb II, whereas animal RV are primarily Sb I. Protein VP6 is highly immunogenic; naturally infected humans and animals develop a strong humoral response against VP6 epitopes. Regardless of the above-mentioned subgroups, VP6 is a highly conserved protein within all the Group A RV (>90% amino acid homology), and the shared common antigens may be detected by broadly reactive polyclonal antisera or monoclonal antibodies. Therefore, VP6 is the target antigen in most immunodiagnostic tests designed to detect Group A RV. The antibodies directed against this protein do not have neutralising activity in vitro. However, IgA monoclonal antibodies manage to block viral replication intracelullarly in mice.

Currently, the prevention of RV-induced diarrhoea in animals is based on passive immunisation, whereas active immunisation is used in human beings. In animals, parenteral inactivated virus vaccines are applied in pregnant females, in order to protect the neonates through the transfer of maternal antibodies via the colostrum and the milk. This strategy is highly effective in preventing the symptoms of severe diarrhoea and in reducing the morbidity and mortality in the affected stocks, but it is not capable of preventing RV infection because it does not significantly reduce the amount of virus excreted by the infected animals (Parreno, V. C. et al., Vet Immunol Immunopathol 100:7-24, 2004). Only the continued presence of high titres of passive anti-RV antibodies in the intestinal lumen (naturally produced or artificially added to the milk) completely protects against diarrhoea and significantly reduces viral excretion (Fernandez, F. M. et al., Vaccine 16:507-16, 1998; Saif, L. J. et al., Infect Immun 41:1118-31, 1983, and Saif, L. J. et al., Adv Exp Med Biol 216B:1815-23, 987).

In children, two live virus vaccines attenuated by genetic reassociation have been approved. Both products have proven good efficacy against severe RV-induced diarrhoea. However, given the history of intussusception associated with a vaccine previously used in humans (Murphy, T. V. et al., J Infect Dis 187:1309-13, 2003) and the recent discovery of RV viraemia in naturally infected children (Ray, P. et al., J Infect Dis 194:588-93, 2006, and Blutt, S. E. et al., Lancet 362:1445-9, 2003), the innocuousness of said vaccines has been called into question, specially in premature, immunosuppressed and malnourished children. Therefore, alternative, complementary strategies are needed for the prevention and treatment of RV-induced diarrhoea.

Passive immunity strategies, such as breastfeeding, the administration of anti-RV antibodies purified from bovine colostrum or eggs (human and bovine anti-RV IgG and chicken egg yolk IgY), were shown to reduce diarrhoea disease in both humans and animals. But the possibility of producing large quantities of antibodies in a cost-efficient manner, and with reproducible properties, is low. Therefore, it is necessary to generate antibodies designed for passive anti-RV immunisation in animals and human beings, particularly antibodies that may be produced at industrial scale, that do not cause immunological reactions, that are sufficiently small to efficiently access the epitopes of conserved internal proteins, and that are capable of recognising and inhibiting the replication of strains from different genotypes (polyreactive).

The VHH domain of the camelid antibody heavy chain is, with a weight of 15 kDa, the smallest known natural domain with complete antigen-binding capacity, is ideal to generate encoding DNA libraries for single-chain fragments with a natural antigen recognition capacity. Moreover, strategies to immunise llamas may be used to enrich the VHH library in those directed against an antigen of interest. Due to its particular properties, VHH domains derived from llama antibody heavy chains are very versatile tools for the development of diagnostic reagents and products designed to prevent or treat RV-induced diarrhoea. For example, a VHH directed against a G3 G-type RV strain, produced in yeasts, has recently been reported to show neutralising activity in vitro, and the purified VHH was capable of reducing the occurrence and the duration of RV-induced diarrhoea in lactating mice (Pant, N. et al., J Infect Dis 194:1580-8, 2006, and van der Vaart J. M. et al., Vaccine, May 8, 24(19):4130-7, 2006). However, these authors have not been able to identify against which viral protein the VHH obtained are directed and they assume that they would be directed against conformational epitopes of external proteins.

Patent document WO 2006/056306 discloses the production and use of VHH domains or fragments thereof as a therapy for infections produced by entero-pathogenic microorganisms, for example RV. It shows the production of said VHH or the use thereof in a specific-site release system. For example, it discloses the release of the specific VHH in the gastrointestinal system by encapsulation in alginate. Moreover, as a release method it proposes the use of transgenic probiotic microorganisms which release the specific VHH antibodies and wherein said microorganisms may colonise the human intestine. It proposes different strategies to prepare drugs or foods using VHH antibodies that are encapsulated or expressed by probiotic microorganisms. The VHH produced do not bind to VP6, would not be neutralising, and are also not used by themselves, but within a controlled-release system.

Patent document US 20050054001, by Muyldermans Serge, discloses heavy-chain antibodies, functional domains of heavy-chain antibodies, functional VH domains or fragments thereof which comprise certain modified or mutated amino acid sequences. It does not disclose sequences that correspond to VHH domains which bind to RV VP6.

Patent document WO 00/65057 discloses monovalent proteins that comprise a single variable domain, which bind to viral antigens, particularly bacteriophage P2 of *Lactococcus*. It only discloses VHH sequences that inhibit said bacteriophage.

Patent document US 2007/0009512, by Hamers et al., and previous documents by the same inventors, disclose heavy-chain fragments of immunoglobulins and the use thereof for veterinary treatments, for example passive immunotherapy or serotherapy. The VHH described only recognise the tetanus toxin. The method used to obtain the VHH is from immunised camelids' mRNA.

BRIEF DESCRIPTION OF THE INVENTION

One object of this invention is to provide a monomeric domain (VHH) derived from camelid antibodies, wherein said domain may be one of the amino acid sequences shown in SEQ ID No. 1, SEQ ID No. 2, SEQ ID No. 3 or SEQ ID No. 4, and wherein said domains bind to protein VP6 of group A RV.

Another object of this invention is to provide a dimeric domain that binds to protein VP6 of group A RV, wherein said fusion protein comprises at least one monomer sequence shown in SEQ ID No. 1, SEQ ID No. 2, SEQ ID No. 3 or SEQ ID No. 4. In a preferred embodiment, the fusion protein comprises the amino acid sequence shown in SEQ ID No. 9, SEQ ID No. 10, SEQ ID No. 11 and SEQ ID No. 12.

Another object of this invention is to provide a rotavirus immunodetection method that comprises bringing into contact an RV-containing sample with one of the amino acid sequences shown in SEQ ID No. 1, SEQ ID No. 2, SEQ ID No. 3, SEQ ID No. 4, SEQ ID No. 6, SEQ ID No. 7, SEQ ID No. 8, SEQ ID No. 9 or combinations thereof; and developing.

Said immunodetection method can be carried out by any of the techniques known in the state of the Art, for example: immunocapture based tests ELISA, ELISPOT, competition ELISA, magnetic beads or pen-side.

Another object of this invention is to provide a composition that confers passive immunity to a mammal, which comprises any of the sequences shown in SEQ ID No. 1, SEQ ID No. 2, SEQ ID No. 3, SEQ ID No. 4, SEQ ID No. 6, SEQ ID No. 7, SEQ ID No. 8 or SEQ ID No. 9, excipient and immunomodulators.

Another object of this invention is to provide a prevention method against infections produced by RV which comprises administering an effective quantity of any of the sequences shown in SEQ ID No. 1, SEQ ID No. 2, SEQ ID No. 3, SEQ ID No. 4, SEQ ID No. 9, SEQ ID No. 10, SEQ ID No. 11, SEQ ID No. 12 or combinations thereof to a mammal that needs it, wherein said sequences are by themselves or combined with substances that encapsulate and protect them from degradation in the gastrointestinal tract.

Another object of this invention is to provide a treatment method for infections produced by RV, wherein said method comprises administering an effective quantity of any of the amino acid sequences shown in SEQ ID No. 1, SEQ ID No. 2, SEQ ID No. 3, SEQ ID No. 4, SEQ ID No. 9, SEQ ID No. 10, SEQ ID No. 11, SEQ ID No. 12 and combinations thereof to a mammal that needs it, by themselves or combined with substances that encapsulate and protect the antibodies against degradation in the gastrointestinal tract.

DESCRIPTION OF THE FIGURES

FIG. 3. VHH-ELISA: Detection of rotavirus strains with different subgroup reactivity and G/P type specificities from different animal species.
A) Antibody-captured monomeric VHH 2KA4, 2 KD1, 3A6 (2 μg/well).
B) Direct coating with bivalent VHH biv2KA4, biv2 KD1, biv3A6 (1 μg/well). Tissue culture supernatant of bovine rotavirus IND (SbI; P[5]G6), C486 (SbI; P[1]G6) and B223 (SbI; P[11]G10); human rotavirus Wa (SbII; P[8] G1) and equine rotavirus H2 (Sb no I, no II; P[12]G3); Positive faeces: faecal sample corresponding to the peak of virus shedding of a calf experimentally infected with bovine rotavirus IND; MA-104: supernatant of mock infected cells. PBS: (blank of reaction), negative faeces: calf faecal sample negative for rotavirus.

Error Bars Indicated Standard Deviation of Two Independent Measurements

Figure 4:
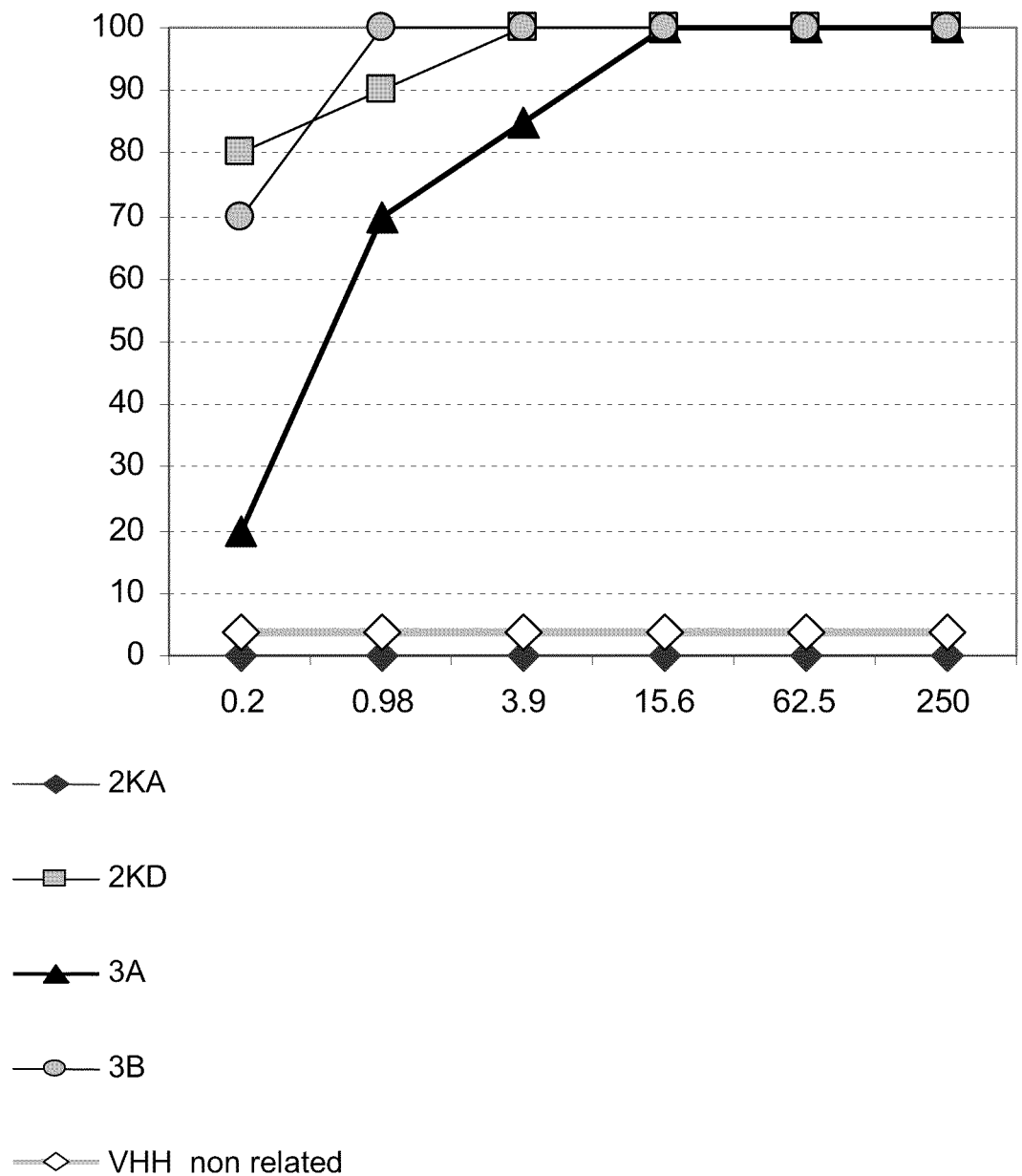

FIG. 4. In vitro rotavirus fluorescent focus reduction assay. A four-fold dilution of each monovalent VHH 2KA4, 2 KD1, 3A6 and 3B2 was mixed with the same volume of rotavirus containing 100 FFU. The VHH concentration that generates >80% reduction of the infection rate is considered as protective.
A. Bovine rotavirus C486 (homologous to Ag used in vaccination and mice challenge);
B. Bovine rotavirus IND (homologous to Ag used in binder selection);

C. Bovine rotavirus B223;
D. Human rotavirus Wa;
E. Equine rotavirus H2.

The graphs represent the summary results of two independent assays.

Figure 5:
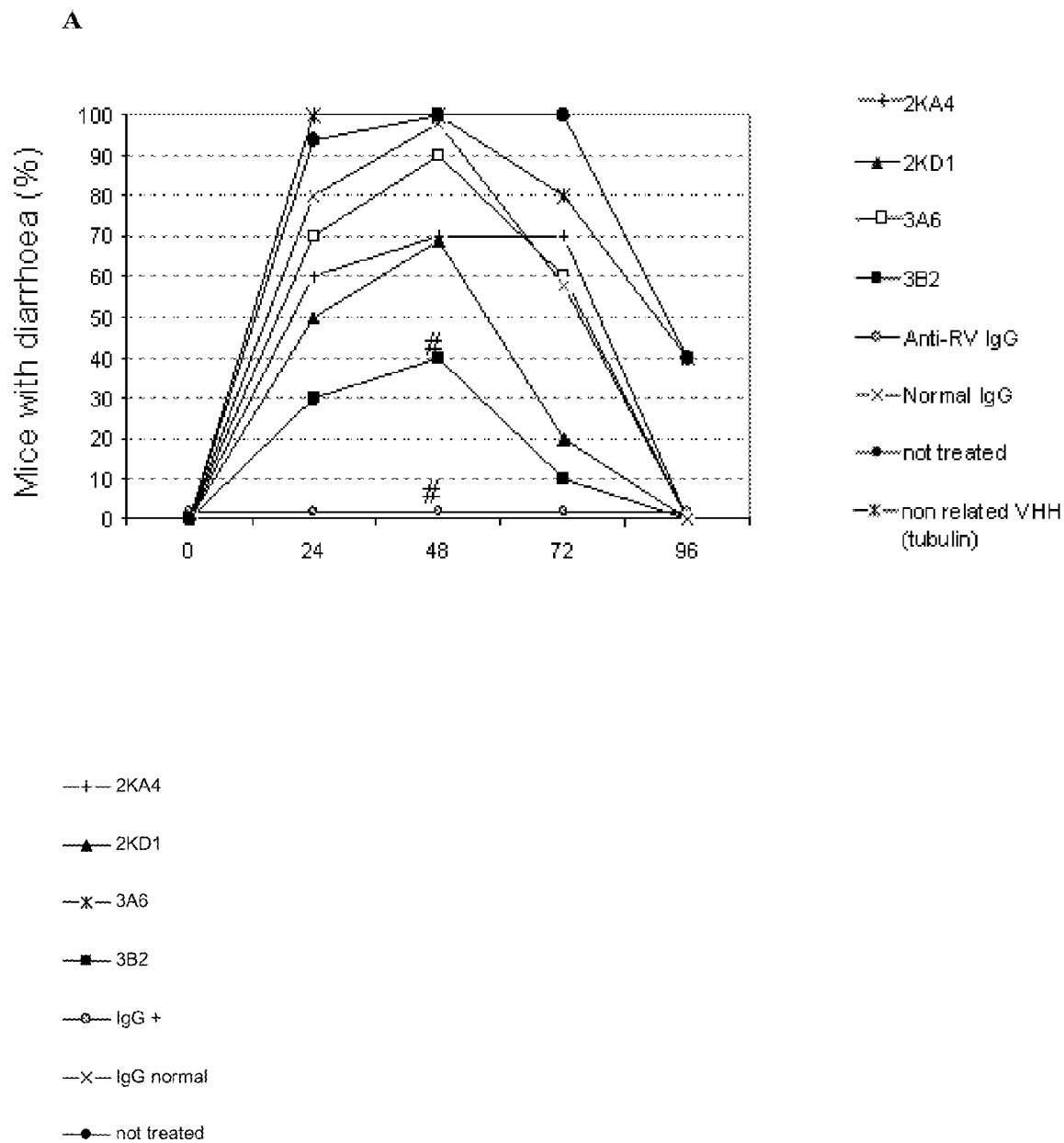

FIG. 5. Protection rate against diarrhoea achieved by monovalent VHH 2KA4, 2 KD1, 3A6 and 3B2 in neonatal mice challenged with rotavirus. Pups were fed with 100 μg (100 μl) of each VHH from day 0 to 5, once a day by intragastric route. At day 1 pups were challenged intragastrically with RV 2 hour after routine feeding. Diarrhoea was followed daily up to 96 hs post challenge.
 A. Challenge: 30 DD50 (6×105 FFU) of bovine rotavirus C486. Experiment was carried out in three independent assays of 5 mice per group.
 B. Challenge: 316 DD50 of murine rotavirus ECw. Experiment was carried out in two independent assays of 5 mice per group.
 C. Virus shedding quantificated by ELISA in the 10% w/v small intestine homogenates.

The symbol # means the percentage of affected animals that differs significantly from the non treated/challenged group, Fisher Exact Test, p<0.05.

Bars represent the average of the ELISA absorbances at 405 nm per group. Error bars indicate ±Standard Deviation. ELISA cut off value: 0.200.

Figure 6A:
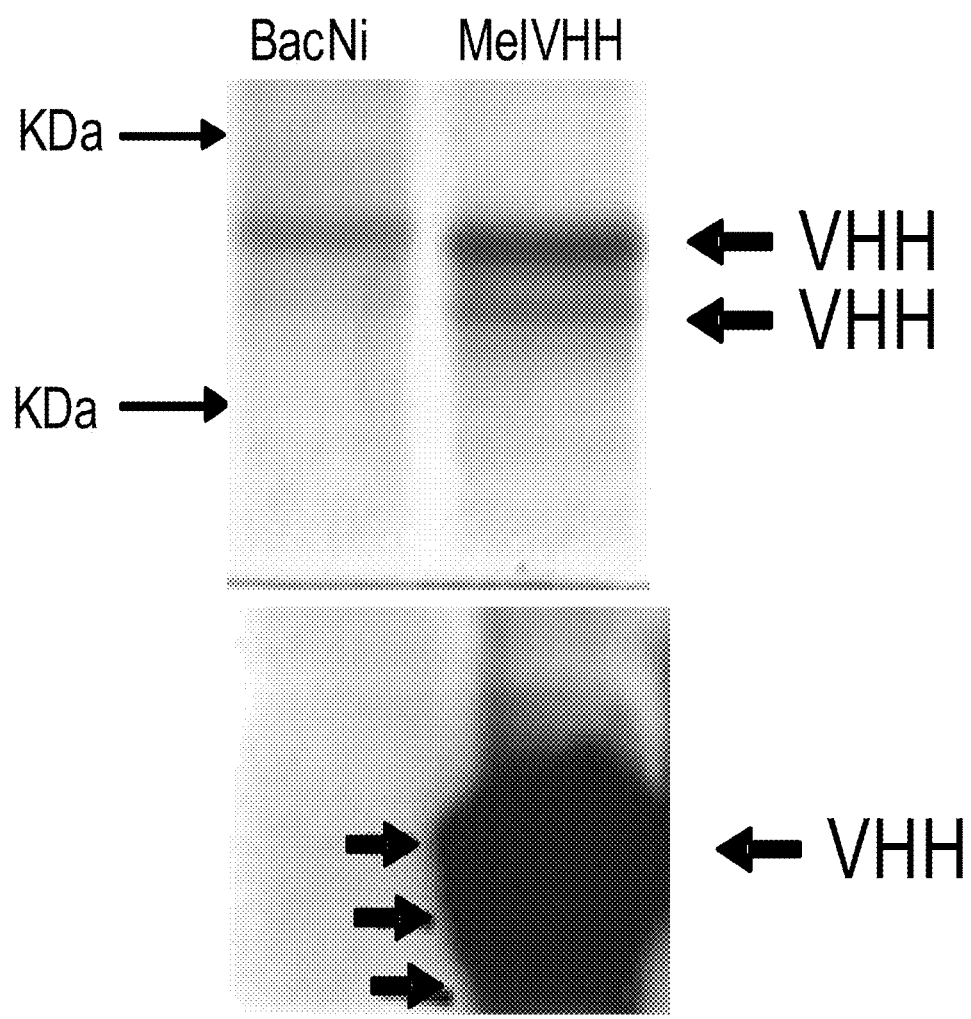
Figure 6B:
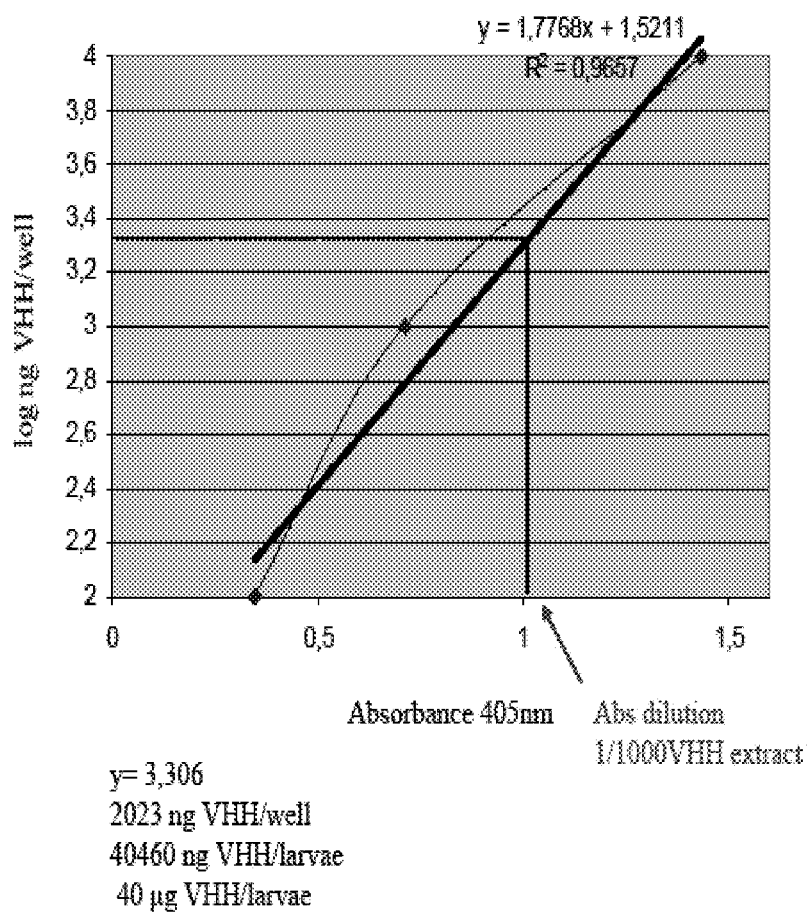

FIG. 6 A. shows the expression of VHH in T.ni larvae. The expression levels are high enough to detect two bands of the expected molecular weight in the coomassie staining. B. shows a quantification of the VHH expressed in the larvae system.

Figure 7:
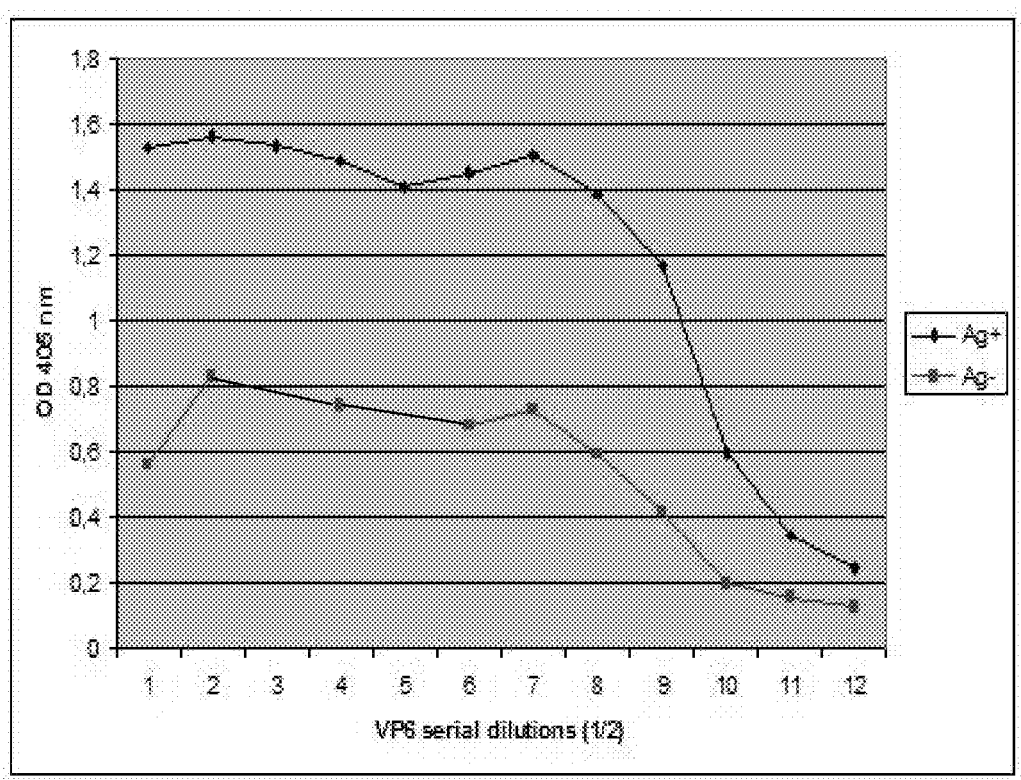

FIG. 7 shows ELISA technique using VHH from larvae. Total soluble proteins (TSP) extracts from VP6 expressing larvae [Ag(+)] or from infected larvae with a Non-insert recombinant baculovirus [Ag(−)] were used to coat ELISA microplates (Polysorp, Nunc, Denmark) with serial dilutions starting at 40 μg/well in 50 mM carbonate/bicarbonate buffer, pH 9.6 and incubated O.N at 4° C.

DETAILED DESCRIPTION OF THE INVENTION

For purposes of this application, the term "domain" is a part of protein (antibody) sequence and structure that can evolve, function, and exist independently of the rest of the protein chain. Each domain forms a compact three-dimensional structure and often can be independently stable and folded. Many proteins consist of several structural domains. One domain may appear in a variety of evolutionarily related proteins. Domains vary in length from between about 25 amino acids up to 500 amino acids in length. The domains are able to bind epitopes. The domains of the present application bind to protein VP6 of group A RV.

For purposes of this application, the terms "VHH", "VHH domain", "monomeric VHH" and "VHH monomer" are considered to have the same meaning and to be interchangeable.

For purposes of this application, the terms "protein VP6", "antigen VP6" and "VP6" are considered to have the same meaning and to be interchangeable.

For purposes of this application, the terms "dimeric domain", "VHH dimers" and "dimeric VHH" are considered to have the same meaning and to be interchangeable.

The term "homodimer" is defined as a protein or polypeptide formed by two identical monomeric domains, with or without a linkage sequence.

The term "heterodimer" is defined as a protein or polypeptide formed by two different monomeric domains, with or without a linkage sequence.

The expression "appropriate growing conditions" refers to the suitable environment stablished in order to improve the growth of the transgenic cells (transformed, transfected or infected by the vector defined in the invention). For example, the infected larvae are kept in growth chambers at 28° C. and collected at indicated times.

For the purpose of the present invention "vaccine" is a preparation which is used to import immunity to a particular disease. A composition designed to confer passive immunity to a mammal, characterised in that it comprises an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof; excipient and immunomodulators.

The expression "effective quantity of an amino acid sequence (polypeptide)" to be administered in a mammal to prevent the infection produced by RV, refers to a pre-estimated amount of the amino acid sequence (polypeptide) needed to bind the epitope and block the action of the pathogen (virus) that eventually will infect the host organism.

The expression "effective quantity of an amino acid sequence (polypeptide)" to be administered in a mammal for treating the infection produced by RV, refers to the amount of the amino acid sequence (polypeptide) needed to bind the epitope and block the action of the pathogen which has already infected the host organism.

For the purposes of the present invention the term "mammal" refers, in general, to members of the Class Mammalia, for example: human beings, bovines, caprines, ovines, swines and equines.

A linkage sequence is defined to be an amino acid sequence that links two monomeric domains.

The selection, obtainment and characterisation of VHH antibodies directed to the intermediate capsid protein of the group A RV, VP6, is described. It is shown that the VHH of the invention are broadly reactive proteins which may be manipulated to be used in a universal immunodiagnostic assay for the detection of group A RV. Moreover, it is shown that some of the selected anti-VP6 VHH have broad neutralising activity in vitro, and that some of said VHH protect against viral challenge in vivo. On the basis of their knowledge, the inventors believe that the VHH of the invention are the first molecules to be described which bind to protein VP6 and have neutralising activity.

Figure 1:
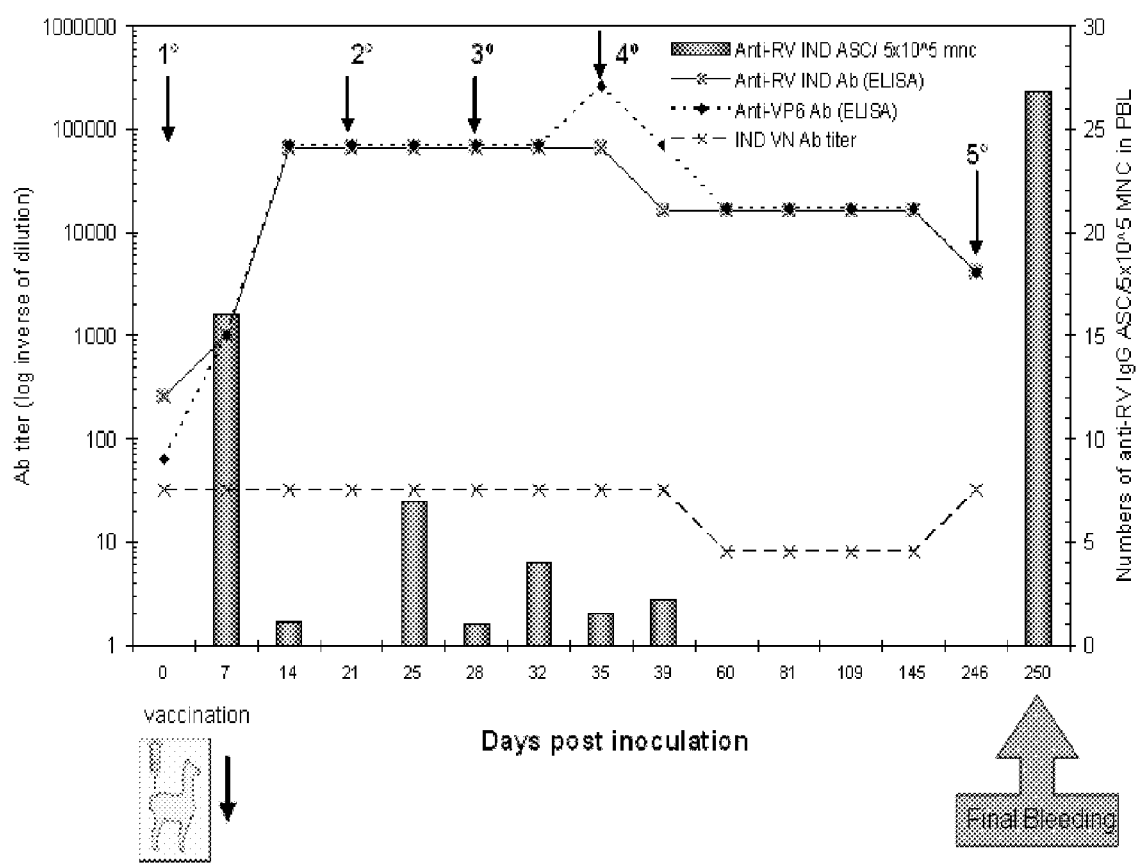
FIG. 1. Llama immunization. Schedule for immunization, sample collection, final bleeding and evaluation of rotavirus antibody response in serum during the time course of immunization: antibody titers measured by (i) ELISA using recombinant VP6, (ii) ELISA using rotavirus (IND; Sb I P[5]G6), (iii) virus neutralization and (iv) ELISPOT using the same rotavirus (IND; Sb I P[5]G6). Vaccination time points are represented by arrows.

In order to obtain the VHH domains of the invention, the animal immunisation schedule shown in FIG. 1 was performed. In order to evaluate the llama's immune response, the anti-RV and anti-VP6 antibody titres were analysed by ELISA, virus neutralisation (VN) assays, and the specific antibody-secreting cells circulating in peripheral blood were analysed by ELISPOT. As expected, on day 0 post-innoculation (DPI), the llamas were positive for anti-RV antibodies, indicating previous contact with the antigen. However, there were no antibody-secreting cells circulating in blood. On day 7 post-injection, the anti-IND-RV or anti-VP6 antibody titre determined by ELISA was high and a peak of RV-specific antibody-secreting cells was detected in peripheral blood (16 cells producing anti-RV IgG/5×10$^5$ mononuclear cells). The humoural response reached a plateau from day 14 post-injection, with high antibody titres for both the whole virus and protein VP6. On the contrary, the neutralising antibody titres remained similar and very low for all the different RV studied (IND, B223, Wa and H2). Although very high antibody titres were obtained in serum, the quantity of anti-RV antibody-secreting cells detected in blood decreased with each booster (FIG. 1). For this reason, and in order to provide enough time to favour antibody affinity maturation, the llama did not receive the final VP6 dose until much later, on day 246 post-injection (approximately 7 months after the 4th dose). Finally, the llama was bled 4 days after the last booster, reaching values of 26.8 anti-RV IgG secreting cells/$5 \times 10^5$ mononuclear cells. $6 \times 10^8$ mononuclear cells were extracted from 900 ml of blood (which contained at least 32,160 RV-specific IgG antibody-secreting cells, according to the ELISPOT results). From the RNA processed (210 µg), a VHH phage library was generated which contained $6 \times 10^7$ clones. The vaccination scheme used showed that, in order to obtain the VHH of the invention, it is more important to achieve high values of specific antibody-secreting cells rather than high antibody titres directed against the antigens of interest. In the vaccination scheme used, it was possible to obtain sufficient quantities of specific antibody-secreting cells. The results obtained during the immunisation allow us to highlight that the best method to follow an immunised llama's immune response, in order to build a VHH library, is to select a technique that evaluates the quantity of specific antibody-secreting cells circulating in peripheral blood, instead of the serum antibody titres against the antigen of interest. According to the pattern of antibody-secreting cells obtained, it was shown that a vaccination scheme with a long interval between the last two doses promotes the circulation of a greater quantity of specific antibody-secreting cells in peripheral blood. It was also shown that, at 4 days post-innoculation, there is a greater number of circulating antibody-secreting cells against the antigen of interest than at 7 days post-innoculation. The immunisation scheme should be performed in such a way that the booster dose is applied to the llamas at least 5 months after the last dose and the phage colonies are generated when a quantity of about 20 anti-target antigen IgG antibody-secreting cells is achieved in peripheral blood. Preferably, for anti-VP6 VHH, the quantity of IgG antibody-secreting cells in peripheral blood must be about 30 anti-complete-rt IgG antibody-secreting cells. Those skilled in the art know that other immunisation schemes may be used to obtain suitable VHH for the methods and compositions of this invention.

In order to select the phages that expressed anti-RV VHH, three selection rounds were performed in vitro using RV IND as the antigen. 192 clones were selected. Restriction analyses were performed for all the clones that showed a large VP6-binding diversity in the VHH library; this was determined by phage ELISA. The clones were also assayed by ELISA to determine their capacity to bind to an RV and to VP6. From 14 clones with different sequences, 10 clones were selected which showed stronger specific binding to RV and VP6, and they were sub-cloned in an expression vector that provides a carboxy-terminal hexahistidine tag to facilitate the purification thereof (Table 1).

TABLE 1

Summary of the results of the qualitative evaluation to select the VHH domains

| VHH monomers | Biopanning round/ condition | RV Phage ELISA | VP6 Phage ELISA | Expression test | | RV detection by ELISA | |
|---|---|---|---|---|---|---|---|
| | | | | Culture appearance | Expression level | VHH as capture[1] | VHH as secondary antibody |
| 2RE4 | 2nd A | ++ | + | normal | +++ | ++ | +++ |
| 2KA4 | 2nd B | +++ | +++ | normal | +++ | ++ | +++ |
| 2KA5 | 2nd B | +++ | − | Lysis | + | ++ | +++ |
| 2KA10 | 2nd B | +++ | +++ | Lysis | Not purified | ++ | +++ |
| 2KD1 | 2nd B | +++ | +++ | normal | +++ | ++ | +++ |
| 3A6 | 3rd B | ++ | + | normal | +++ | ++ | +++ |
| 3B2 | 3rd B | +++ | ++ | normal | ++ | ++ | +++ |
| 3C10 | 3rd B | +++ | − | normal | ++ | ++ | +++ |
| 3D9 | 3rd B | +++ | +++ | normal | +++ | ++ | background |
| 3H1 | 3rd B | +++ | − | Lysis | Not purified | ++ | +++ |

[1]Bound to the plate using anti-histidine antibody.

Figure 2:
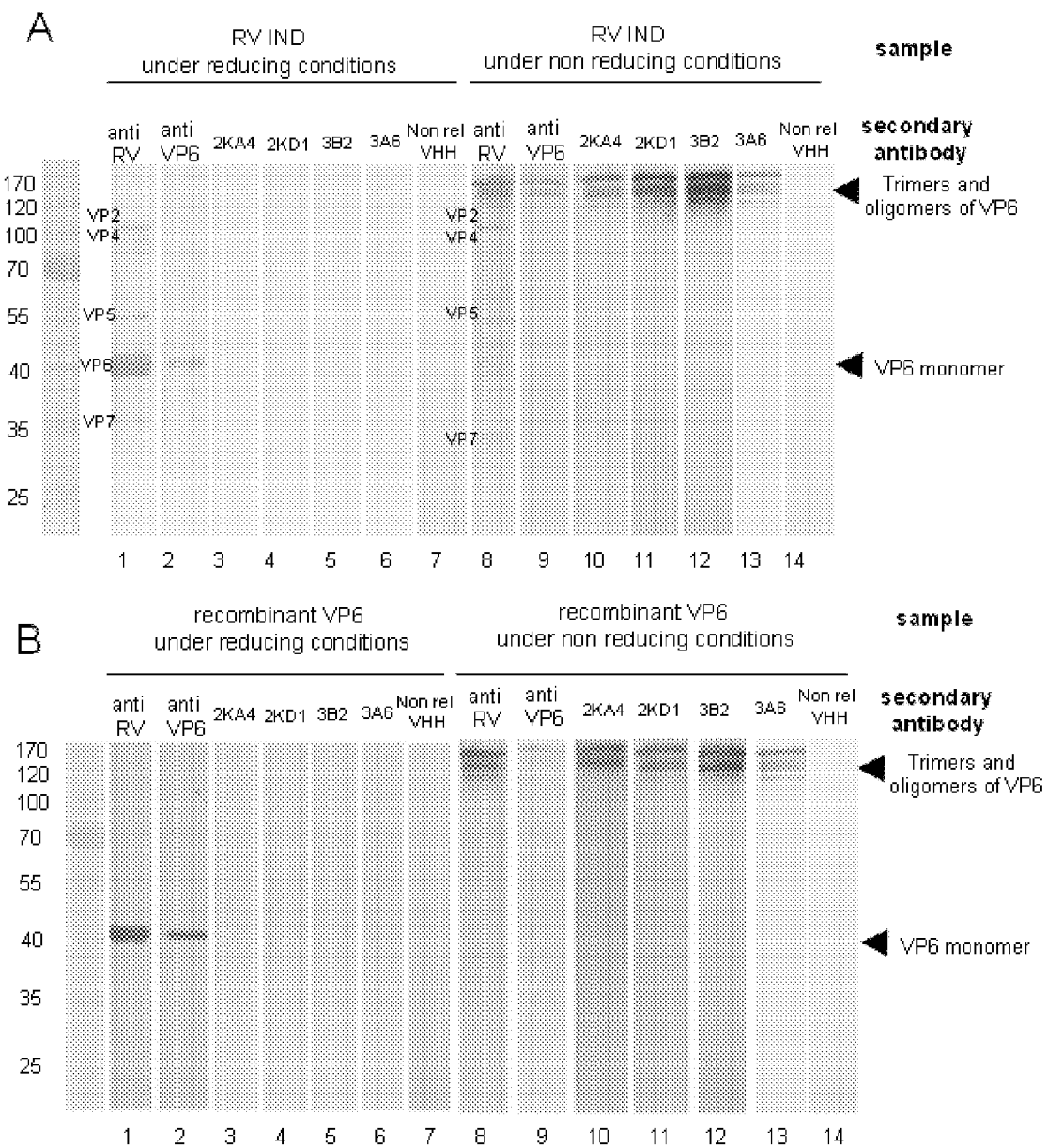
FIG. 2. Detection of native and recombinant VP6 protein by Western blot analysis. BRV IND (A) or recombinant VP6 (B) run under reducing conditions; or under non reducing conditions and detected with: Lanes 1 and 8-Bovine Polyclonal serum anti-group A RV; 2 and 9-Anti VP6 Mab (RG25A10); 3 and 10-VHH 2KA4 anti VP6; 4 and 11-VHH 2 KD1 anti VP6; 5 and 12-VHH 3B2 anti VP6; 6- and 13 VHH 3A6 anti VP6; 7 and 14-non related VHH.

Four clones were selected which bound more strongly to the RV strains that corresponded to different subgroups; these clones were called 2KA4 (SEQ ID No. 1), 2 KD1 (SEQ ID No. 2), 3A6 (SEQ ID No. 3) and 3B2 (SEQ ID No. 4), which recognised a recombinant VP6 and its native counterpart of RV IND evaluated by Western Blot, which indicates that said VHH bind to conformational epitopes of this protein VP6 (FIG. 2). Hereinafter, the VHH called 2KA4, 2 KD1, 3A6 and 3B2 are the VHH domains of the invention.

The DNA sequences that encoded each of the VHH domains were the following:
SEQ ID No. 5 encodes the SEQ ID No. 1 domain;
SEQ ID No. 6 encodes the SEQ ID No. 2 domain;
SEQ ID No. 7 encodes the SEQ ID No. 3 domain;
SEQ ID No. 8 encodes the SEQ ID No. 4 domain;

Those skilled in the art know that any DNA sequence that encodes said domains falls within the scope of this invention. For example, amino acid sequence SEQ ID No. 1 may be encoded by DNA sequence SEQ ID No. 5 or another DNA sequence that differs from SEQ ID No. 5 due to the degeneration of the genetic code. The same example is valid for each of the amino acid sequences (SEQ ID No. 2, 3 and 4) encoded by the respective DNA sequences (SEQ ID No. 6, 7 and 8).

Figure 3:
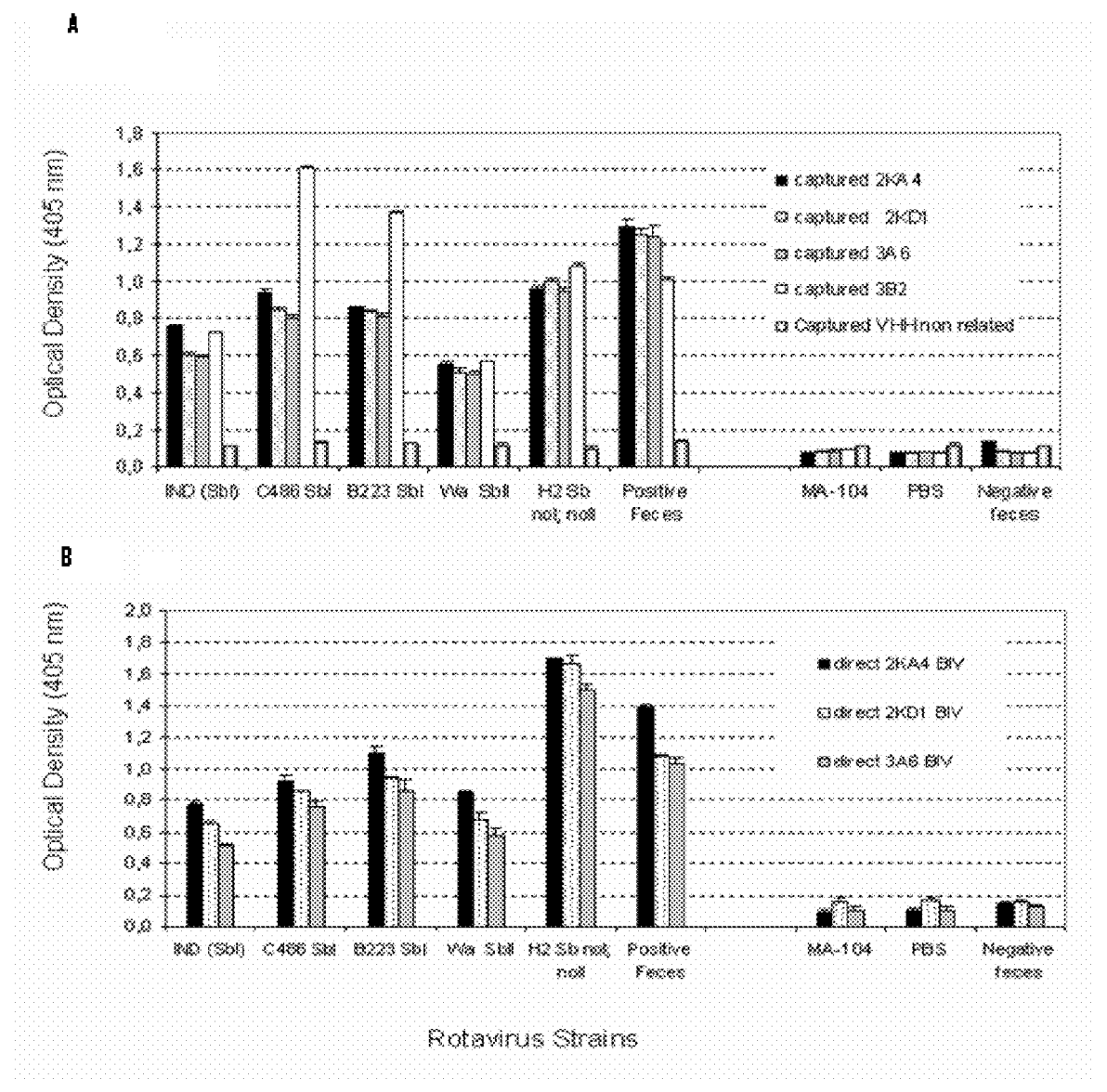

The anti-VP6 specific VHH of the invention were very efficient as reagents for the immunodiagnosis of RV. The monomeric forms of the VHH of the invention were assayed in ELISA as capture antibodies, as secondary antibodies or immobilised by means of anti-His antibodies. The VHH of the invention were capable of detecting RV strains of human or animal origin with different specific subgroups and different G and P types (FIG. 3A).

On the other hand, expression vectors were constructed to produce the dimeric VHH of the invention that specifically bind to VP6, which constitute identical VHH genes bound to a linkage sequence similar to the human IgA hinge sequence. The dimeric VHH of the invention were also evaluated in ELISA as direct capture, showing clear, reproducible signals for all the RV strains studied (FIG. 3B). The dimeric VHH of the invention may be used for ELISA plate sensitisation, thus eliminating the need to use VHH capture antibodies and show better results for RV detection than their monomeric counterpart.

It is worth highlighting that the yields of monomeric VHH expressed in the periplasma of *E. coli* were comparable to those reported by other authors in *E. coli* and yeasts.

The monomeric and dimeric VHH of this invention have proven to be very useful for the diagnosis of RV and, therefore, may be used as recombinant monoclonal antibodies in any immunodiagnosis known by those skilled in the art. It is evident for those skilled in the art that the monomeric and dimeric VHH domains of the invention may be used for any type of immunodiagnosis assay to detect RV, and that said assays fall within the scope of this invention.

The anti-VP6 domains of the invention may be used to construct dimers such as those described herein, for example homodimers, or may be fused to form heterodimers, for example by fusing domain 3B2 and domain 3A6, or fusing any two of the VHH monomers of the invention. Furthermore, three or more VHH monomers of the invention may also be fused or combined to generate homotrimers or heterotrimers. All the multimeric forms that arise from the combination of VHH monomers of the invention, whether or not they contain a linkage sequence, fall within the scope of this invention. In a preferred embodiment, the VHH dimers of the invention have the sequences disclosed as SEQ ID No. 9, or SEQ ID No. 10, or SEQ ID No. 11, or SEQ ID No. 12. For example, the dimers may comprise an amino acid linking sequence, such as that shown in SEQ ID No. 13, or any other sequence that acts as a hinge sequence.

The following Table shows some characteristics of the dimeric and monomeric VHH of the invention.

TABLE 2

| | Characteristics | | | |
|---|---|---|---|---|
| | Protein specificity[1] | Large-scale production yield (mg/l)[2] | Poly-reactive for RV (ELISA)[3] | Neutralisation of RV infectivity in vitro (□g/100 FFU RV) |
| Monomers | | | | |
| 2KA4 | VP6 | 52.1 | yes | NO |
| 2KD1 | VP6 | 21.3 | yes | High |
| 3A6 | VP6 | 18.6 | yes | Medium |
| 3B23 | VP6 | 16.9 | yes | High |
| non-related | Cellular protein | 7.2 | NO | NO |
| VHH Dimers | | | | |
| Biv2A4 | NA | 0.90 | yes | NO* |
| Biv2KD1 | NA | 0.50 | yes | Low |
| Biv3A6 | NA | 1.72 | yes | Low and strain-dependent |

[1] Determined by WB against RV IND and recombinant VP6.
[2] Based on a set of 6 cultures of 0.5 l each, purified by means of an anti-histidine tag column.
[3] Detection of RV strains Sb I, Sb II, Sb no I; no II.

The anti-VP6 VHH domains of the invention were capable of neutralising different RV strains in vitro. Three of the four monomers of the invention (2 KD1, 3A6 and 3B2) showed broadly neutralising activity in vitro. The neutralising capacity of each VHH was homogeneous for all the RV strains evaluated. Monomer concentrations from 3.9 µg/ml were capable of completely neutralising the infectivity generated by 100 FFU of RV strains C486 (P[1]G6), IND (P[5]G6), B223 (P[11]G10), Wa P[8]G1 and H2 (P[12]G3), in vitro. Table 3 lists the neutralisation titre against different RV strains of a solution with a concentration of 2 mg/ml for each monomer.

TABLE 3

Neutralisation titre of the different monomeric and dimeric VHH domains

| | | VN antibody titre[1] | | | | |
|---|---|---|---|---|---|---|
| VHH Domain | VHH concentration assayed | IND SbI P[5]G6 | C486 SbI P[1]G6 | B223 SbI P[11]G10 | Wa SbII P[8]G1 | H2 Sb noI, noII P[12]G3 |
| Domain | | | | | | |
| 2KA4 | 2 mg/ml | <8 | <8 | <8 | <8 | <8 |
| 2KD1 | | 2048 | 2048 | 2048 | 8192 | 512 |
| 3A6 | | 1024 | 1024 | 256 | 2048 | 128 |
| 3B2 | | 1024 | 1024 | 2048 | 8192 | 512 |
| Non-related VHH | 0.4 mg/ml | <8 | <8 | <8 | <8 | <8 |
| Dimers | | | | | | |
| Biv2KA4 | 0.5 mg/ml | <8 | <8 | <8 | 32 | <8 |
| Biv2KD1 | 0.5 mg/ml | 32 | 128 | 8 | 128 | 32 |
| Biv3A6 | 2 mg/ml | 128 | 512 | 8 | 512 | 128 |

[1] Neutralising antibody titres for different RV strains, expressed as the inverse of the highest VHH dilution that reduces >80% of the focus-forming units generated per 100 FFU of each RV strain.

Therefore, the VHH monomers were capable of neutralising RV strains belonging to different combinations of G/P types that normally do not induce cross-neutralisation. The VHH monomer with the greatest neutralisation capacity was monomer 2 KD1. On the other hand, although monomer 2KA4 was capable of appropriately recognising all the RV in ELISA, it did not neutralise any of the strains studied. The capacity of the VHH of the invention to neutralise high titres of antigenically different RV strains is of great significance and would make them poly-neutralising molecules; this property makes them potential prevention or treatment tools for RV-induced diarrhoea regardless of the serotype (27 P-types and 16 G-types)

The dimeric VHH showed less neutralisation activity than their monomeric counterparts.

The capacity of the VHH monomers of the invention to treat and prevent diarrhoeae produced by RV infection was evaluated. To this end, neonatal mice were administered a daily intragastric dose of VHH for 5 days (day 0 to 4). The mice were challenged on day 1 with viral strain C486, also by intragastric route (FIG. 5). 60% of the mice treated with monomeric VHH of the invention 3B2 were protected against RV-induced diarrhoea. This protection was significantly greater when a comparison was made between the treated mice and the untreated mice or those treated with non-related VHH ($p=0.0108$), wherein all the mice suffered from diarrhoea (Table 4 and FIG. 5). Moreover, the severity and the duration of the diarrhoea in the animals treated with the VHH of the invention were significantly reduced as compared to the control groups.

production costs. This is particularly relevant in developing countries, where the magnitude of infection and the morbility/mortality due to RV is enormous, and treatment and prevention costs are critical limiting factors.

Any person skilled in the art knows that, on the basis of what is disclosed herein, the VHH domains of the invention may be produced by synthesis of the corresponding nucleotide sequence and the expression thereof in any host cell, without the need to create a phage library.

It is evident for any person skilled in the art that different combinations and mixtures of the VHH monomers, VHH dimers or VHH multimers of the invention may be used for immunodiagnosis, prevention of RV infections and treatment of mammals infected by RV without altering the spirit of this invention, and wherein all the possible combinations and mixtures fall within the scope of this invention.

Such as it has been mentioned before, four clones were selected which bound more strongly to the RV strains that corresponded to different subgroups. These clones were called 2KA4 (SEQ ID NO: 1), 2 KD1 (SEQ ID NO: 2), 3A6 (SEQ ID NO: 3) and 3B2 (SEQ ID NO: 4), which recognised a recombinant VP6 and its native counterpart of RV IND evaluated by Western Blot, which indicates that said VHH bind to linear epitopes of this protein VP6.

Said domains of the invention (SEQ ID NO: 1 to 4) or the nucleotide sequences codifying for them (SEQ ID NO: 5 to 8) may be inserted in an appropriate recombinant vector, such as an expression vector. Therefore, the present invention further refers to an expression vector that comprises said sequences.

TABLE 4

Protection against the challenge with Rotavirus in lactating mice

| Treatment (100 µg of I.G. VHH once a day for 4 days: 0-5) Challenge on day 1: C486 ($2 \times 10^5$ FFU) | n | Mean duration in the group | Mean severity in the group | Diarrhoea % animals affected | Onset | Mean duration of the diarrhoea in affected animals. | Severity of the diarrhoea in affected animals |
|---|---|---|---|---|---|---|---|
| 2KA4 | 10 | 2 A B | 3.7 B | 80 AB | 1.25 A | 2.5 AB | 4.12 B |
| 2KD1 | 10 | 1.4 B | 3.25 B | 70 AB | 1.28 A | 2.0 B | 3.78 B |
| 3A6 | 10 | 2.2 AB | 4.15 AB | 90 AB | 1.22 A | 2.4 AB | 4.39 AB |
| 3B2 | 10 | 0.8 B | 2.65 B | 40 B | 1.25 A | 2.0 B | 3.62 B |
| Non-related VHH | 5 | 2.4 AB | 4.4 | 100 A | 1.2 A | 2.4 AB | 4.4 AB |
| Positive polyclonal serum | 5 | 0 B | 2.1 B | 0 B | na | na | na |
| Normal polyclonal serum | 5 | 2.4 AB | 4.25 AB | 100 A | 1.2 A | 2.4 AB | 4.25 AB |
| Untreated/ challenged | 15 | 3 A | 5.3 A | 100 A | 1.05 A | 3.3 A | 5.31 A |
| Untreated/not challenged | 5 | 0 B | na | 0 B | na | na | na | na: not applicable

The mean values of the same columns with different letters differ significantly (Kruskal Wallis, $p<0.05$).

The percentages of affected animals with different letters differ significantly (Fisher Exact Test, $p<0.05$).

It is worth noting that the highest neutralisation titre was obtained against the human heterologous RV strain (Wa, SbII, P[8]G1), which is considered to be the strain most commonly associated with gastroenteritis in children worldwide.

The production and purification of these antibody fragments may be performed with high yields, leading to lower The election of the vector is a function of the type of host cell in which the vector is going to be introduced. Illustratively, the vector may be a plasmid or a vector that, once it is introduced in the host cell, is integrated or not in the genome of said host cell. Said vector can be obtained by using any known method comprised in the state of the art [Sambrok et al. 1989]. In a preferred embodiment, the vector of the invention can be used to be inserted in the genome of plant or animal cells. Thus, the vector of the invention can be, for example, *Agrobacterium tumefaciens* or a viral vector able to be expressed in plant or animal cells. In a particular embodiment, the viral vector used in the present invention is Baculovirus (see Example 5).

The vector may be used for transforming, transfecting or infecting plant, algae or animal cells, preferably insect or larvae cells. Therefore, the present invention further refers to the cells transformed, transfected or infected by the vector of the invention.

In a preferred embodiment of the invention, the transgenic cell is an animal cell, preferably a insect cell and more preferably a larvae of said insect cell. Therefore the invention further refers with a transgenic non human animal, such as a transgenic insect or transgenic larvae expressing the peptide characterized by the SEQ ID: 1 to 4 in a high yield.

Therefore the vector of the invention can be used to produce and/or store the domains of the invention characterized by the SEQ ID NO: 1 to 4 and/or 9 to 12. Consequently, the present invention further refers to a method for producing domains of the invention that comprises growing the cell or the organism transfected, transformed or infected with the vector of the invention under conditions that permit the production of said domains. The conditions for optimizing the culture of the transgenic cell or organism will depend on the type of cell or organism used. If it is desired, the method for producing the domains of the invention further comprises their isolation and purification following any of the method known in the art.

In preferred embodiment, the present invention refers to antibodies characterized by comprising any of the domains of the invention:

A monomeric VHH domain derived from camelid antibodies, characterised in that it comprises the sequences selected from the group formed by SEQ ID No. 1, SEQ ID No. 2, SEQ ID No. 3 and SEQ ID No. 4, wherein said domains bind to protein VP6 of group A rotavirus (RV).

A dimeric VHH domain that binds to protein VP6 of group A RV, characterised in that it comprises at least one monomer sequence selected from the group formed by the sequences shown in SEQ ID No. 1, SEQ ID No. 2, SEQ ID No. 3 and SEQ ID No. 4.

Another aspect of the present invention refers to a kit for immunodetection of RV comprising an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof.

The invention further refers to an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof, for use in a method for the prevention of infections produced by RV. In other words, the invention refers to the use of an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof, for the manufacture of a composition for the prevention of infections produced by RV.

Moreover, the invention further refers to an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof, for use in a method for treating infections produced by RV. In other words, the invention refers to the use of an amino acid sequence selected from the group formed by SEQ ID No. 1, SEQ ID No. 2, SEQ ID No. 3, SEQ ID No. 4, SEQ ID No. 9, SEQ ID No. 10, SEQ ID No. 11, SEQ ID No. 12, and combinations thereof, for the manufacture of a composition for treating infections produced by RV.

Finally, the present invention refers to a method for passive immunisation that comprises the inoculation of an effective quantity of the above defined antibodies in the human or animal body.

Deposit of Microorganisms According to the Budapest Treaty

Plasmid pFBMeIVHH (see Example 5) was deposited in the Spanish Type Culture Collection (CECT); University of Valencia, Spain with the accession number CECT7431, on the date Feb. 7, 2008, in accordance with the Budapest Treaty.

EXAMPLES

This invention is best illustrated by the following examples, which should not be interpreted to be a limitation imposed on the scope thereof. On the contrary, it must be clearly understood that other embodiments, modifications and equivalents thereof may be used which this description may suggest to those skilled in the art without moving away from the spirit of this invention and/or the scope of the attached claims.

Example 1

Obtainment and Purification of the Monomeric and Dimeric VHH of the Invention

Obtainment of the VHH Library of the Invention:

The reference bovine IND RV strain was used (SbI; P[5] G6) as an antigen in the biopanning process to select the VHH. In order to have an RV panel that represents different subgroup reactivities with different combinations of G and P types from different animal species and from humans, the reference RV strains listed in Table 4 were included in the different assays performed to produce the VHH. The viruses were propagated in monkey kidney cells (MA-104). Also included was a faecal sample from a colostrum-deprived neonatal calf infected with the IND strain at the time of pre-innoculation and at the peak of virus spreading.

TABLE 5

Reference rotavirus strains used in the different procedures performed during the production and characterisation of the VHH of the invention

| RV Strain | Species of origin | Subgroup | G-P type | Procedure |
| --- | --- | --- | --- | --- |
| C486 | Bovine | I | P[1]G6 | Recombinant VP6 antigen used for vaccination and for specific ELISA Llama antibody response (VN) Binder characterisation (VN, ELISA) Challenge in mice |
| IND | Bovine | I | P[5]G6 | Binder selection (Biopanning; Phage-ELISA Binder characterisation (VN, ELISA) Llama antibody response (VN, ELISA, ELISPOT) |
| B223 | Bovine | I | P[11]G10 | Llama antibody response (VN) Binder characterisation (VN, ELISA) |

TABLE 5-continued

Reference rotavirus strains used in the different procedures performed during the production and characterisation of the VHH of the invention

| RV Strain | Species of origin | Subgroup | G-P type | Procedure |
|---|---|---|---|---|
| Wa | Human | II | P[8]G1 | Llama antibody response (VN) Binder characterisation (VN, ELISA) |
| H2 | Equine | no I; no II | P[12]G3 | Llama antibody response (VN) Binder characterisation (VN, ELISA) |

Inmunisation of the Llamas: Protein VP6 Derived from Bovine RV Strain

C486 (SbIP[1]G6), was produced in Sf9 cells infected with a recombinant baculovirus. A one-year-old male llama received five doses of crude cellular extract containing 500 μg of VP6 mixed with INTA oil adjuvant (Marcol:Arcel:Span:Tween) at days 0, 21, 28, 35 and 246. Serum and blood samples were taken at days 0, 4 and 7 following each innoculation. The humoural response was evaluated by ELISA and viral neutralisation (VN) (see further below). In order to evaluate the effector B-cell response, an ELISPOT assay was adapted which determines the number of RV-specific antibody-secreting cells in peripheral blood of the innoculated llama, on the basis of previous ELISPOT assays performed in pigs and calves (Parreno, V. C. et. al., Vet Immunol Immunopathol 100:7-24, 2004, and Parreno, V. V. et. al., J Vet Med B Infect Dis Vet Public Health 48:713-20, 2001, incorporated herein solely as a reference). Briefly, MA-104 cells infected with BRV IND (with more than 80% infection detected by immunofluorescence) were fixed, grown in 96-well plates, with 70% acetone, air-dried and stored at −20° C. until they were to be used. Suspensions of mononuclear cells (MNC) derived from peripheral blood (PB) of the innoculated llama were added to the wells ($1×10^6$; $5×10^5$; $2.5×10^5$ and $1.25×10^5$ cells/well). After centrifuging at 500 g for 5 minutes, the plates were incubated for 12 to 14 hours at 37° C. in 5% $CO_2$. The plates were washed with PBS with 0.05% Tween-20 in order to remove the adherent cells, and the spots were generated by adding the same conjugate used in ELISA in a 1/1,500 dilution for 2 hours at 37° C., followed by 50 μl of the TMB peroxidase substrate system (KLP, Maryland, USA).

The handling, innoculation and collection of llama samples was performed by trained personnel under the supervision of a veterinarian, in accordance with protocols approved by INTA's animal welfare ethics committee.

Production of the VHH Library and Selection of the VP6-Binding VHH of the Invention:

From a total of 900 ml of blood collected 4 days after the last injection, $6×10^8$ mononuclear cells were extracted by Ficoll Paque gradient centrifugation; they were then centrifuged, frozen in liquid nitrogen and subsequently kept at −80° C. The total RNA was extracted using a RNA extraction equipment (Macherey Nagel; Nucleospin RNA II), obtaining 250 μg of RNA. Subsequently, the first cDNA chain was synthesised using the Superscript III Reverse Transcriptase equipment (Invitrogen), with OligodT (12-18) primers (Invitrogen) or random primers (Invitrogen). In a 20-μl reaction mixture, 0.2, 1 or 5 μg of total RNA were used. The VHH- and VH-encoding cDNA was specifically amplified by PCR using primers CALL01 (SEQ ID No. 14) and CALL02 (SEQ ID No. 15), which anneal with the leader and CH2 sequences.

The 600-pb fragment (exons VHH-CH2 without exon CH1) was eluted from a 1.6% agarose gel, after separating it from the 900-pb fragment (exons VH-CH1-CH2). The VHH were then amplified by an additional nested PCR with primers annealing at framework region 1 (SEQ ID No. 16) and framework region 4 (SEQ ID No. 17), and with primers containing restriction sites for the subsequent cloning steps: VHHfor2: (SEQ ID No. 18), with restriction sites for NcoI and PstI, and VHHrev2 (SEQ ID No. 19), with a restriction site for NotI. The final PCR fragments were ligated using upstream restriction sites NcoI or PstI and downstream restriction site NotI, in phagemid vector pAO-Lib, a modified version of pHEN4 (Arbabi Ghahroudi M, Desmyter A, Wyns L, Hamers R, Muyldermans S. Selection and identification of single domain antibody fragments from camel heavy-chain antibodies. FEBS Lett. 1997 Sep. 15; 414(3):521-6), which contains an irrelevant long sequence that is removed following the insertion of VHH, in such a way so as to delay the potential propagation of the vector without the VHH insert. *Escherichia coli* (TG1) cells were transformed with the ligated material and the cells were seeded. The colonies were scratched from the plates, washed and kept at −80° C. in LB medium supplemented with glycerol (50% final concentration).

The specific VHH were selected from the library using phage display technology. The VHH library was infected with M13 helper phages (Invitrogen), and the phage particles that express the VHH repertoire were rescued and precipitated with PEG, as described by Marks, J. D., Hoogenboom, H. R., Bonnert, T. P., McCafferty, J., Griffiths, A. D., Winter, G. JMB, 1991. The enrichment in specific VHH was performed by two to three selection rounds in vitro, that is, by the technique known as biopanning. Immunotubes were coated overnight at 4° C. with a 1/50 dilution of semi-purified BRV IND (SbI; P[5]G6) or with a 1/5,000 dilution of an anti-RV polyclonal antiserum from guinea pig in carbonate buffer at pH 9.6, followed by a blocking step, and a 1/50 dilution of the same BRV IND was captured. The rescued phages were incubated with the BRV IND, either directly or with that previously captured, washed, and the bound phage particles were eluted with 100 mM triethylamine at pH 10.0 and immediately neutralised with Tris pH 7.4. The eluted phages were used to infect exponentially growing TG1 cells. After the second or third biopanning round, the individual colonies were grown and the corresponding VHH clones were analysed by phage ELISA.

Expression and Purification of the Monomeric and Dimeric VHH of the Invention:

The VHH cDNA of the clones that were positive in ELISA were re-cloned using restriction enzymes NcoI and NotI in expression vector pHEN6 (Conrath, K. E. M. et. al. Antimicrob Agents Chemother 45:2807-12, 2001, incorporated herein solely as reference), which provides a pelB targeting sequence for the periplasma and a carboxy-terminal six-histidine tag. The bivalent VHH were constructed by PCR amplification of the VHH sequence using primers Bivfor2 (SEQ ID No. 20) and Bivrev2 (SEQ ID No. 21) (SEQ ID No. 22), which encode a linker related to the human IgA hinge. The PCR product and the pHEN6 vector containing the VHH template were digested with NcoI and PstI, and ligated to produce vector pAO-biv, which contains the bivalent VHH. In order to produce the monovalent or bivalent VHH, *E. coli* XL1 Blue cells were transformed with the different plasmid constructs. VHH expression was induced with 1 mM isopropyl-D-thiogalactopyranoside for 16 hours at 27° C. (Sambrook, J., and Russell, D. W., 2001, Molecular Cloning). After centrifuging the cells, the periplasmic proteins were extracted by osmotic shock. The VHH were purified from the periplasmic extract using an N-High-Trap HP chelating column (Amersham Biosciences).

Example 2

Characterisation of the VHH of the Invention

Western Blot:

VP6 concentrates expressed in a baculovirus system and BRV IND concentrates were re-suspended in a Laemmli sample buffer, boiled for 10 minutes. They were then run through a 12% SDS-PAGE column and transferred to an Immobilon P membrane (Millipore, Berdford, Mass.). The membrane was blocked for 45 min with PBS/Tween (0.05%), containing 10% skim milk, and each of the VHH (4 µg/ml) were incubated for 2 h at ambient temperature. The membrane was then washed with PBS/Tween (0.05%) and incubated overnight at 4° C. with the anti-pentahistidine antibody (1/500 dilution in PBS/Tween (0.05%) BSA (3%). Finally, they were incubated with HRP-conjugated goat anti-mouse IgG (1/5,000 dilution) (Amersham, Pharmacia, Biotech) for 40 min at ambient temperature. The assays were developed with ECL (Amersham Biosciences).

Sequencing of the VHH of the invention: In order to sequence the VHH, the "M13 forward" and "M13 reverse" oligonucleotides were used, following this method: Big Die Terminator Cycle Sequencing Ready Reaction Kit (Applied Biosystem) in an ABI-Prism 377 DNA automatic sequencer (Perkin Elmer, Applied Biosystems).

Example 3

RV Immunodetection Assays Using the VHH of the Invention

Enzyme Immunoassay (ELISA) and Western Blot:

The ELISA experiments were performed in Maxisorp 96-well plates (Nunc), by direct sensitisation with RV or by capture of RV or of recombinant VP6 with a polyclonal antibody produced in a gnotobiotic pig. As antigens for the negative control, pseudo-infected MA-104 cells and a non-related protein expressed in baculoviruses (protein E2 of the bovine diarrhoea virus) were used. PBS was used as a blank, and non-immunised guinea pig serum was used as a negative capture.

The presence of anti-RV antibodies in the llama serum was analysed as described in Parreno, V. C. et. al., Vet Immunol Immunopathol 100:7-24, 2004, and that of anti-VP6 antibodies was analysed with a protocol adapted from Fernandez et al. (Fernandez, F. M. et al., Vaccine 16:507-16, 1998). The llama IgG were detected using a peroxidase-labelled goat anti-llama IgG (H+L) (Bethyl, lab inc, Montgomery, Calif., USA), in a 1/2,000 dilution.

The phages derived from the individual clones obtained by biopanning were analysed by phage ELISA. Briefly, individual exponentially growing E. coli TG1 clones, containing the different VHH genes in vector phen4, were infected with M13 helper phages in order to produce phage particles that express VHH fused to the surface protein, and the culture supernatant containing the phage progeny was assayed in ELISA plates sensitised with BRV IND or VP6. The bound phages were detected using a 1/5,000 dilution of an HRP-conjugated anti-M13p8 antibody (Amersham, Pharmacia, Biotech) for 40 minutes at ambient temperature. The assays were developed using $H_2O_2$/ABTS (Zymed).

First, the monovalent or bivalent VHH purified with the carboxy-terminal 6-His tag were studied as reagents to detect RV or VP6 by ELISA, as described above, developed by an anti-pentahistidine monoclonal antibody (Qiagen, 1/5,000) and an HRP-conjugated goat anti-mouse antibody. Secondly, these were analysed as an RV capture reagent, both by direct ELISA plate sensitisation of 10 µg/ml of VHH and captured by 10 µg/ml of anti-histidine monoclonal antibody, and, subsequently, 20 µg/ml of VHH. The assays were developed using an RV polyclonal antiserum from a colostrum-deprived calf hyperimmunised with BRV IND (1/2,000 dilution) and a peroxidase-labelled anti-bovine IgG (H+L) (KPL, Gaithersburg, Md., USA) in a 1/5,000 dilution.

The dimeric VHH were tested by ELISA as an RV capture reagent at 10 µg/ml.

The monomeric VHH were also assayed as secondary antibodies and the ELISA was developed with anti-pentahistidine monoclonal antibodies and HRP-conjugated goat anti-mouse antibodies (1:1,000 dilution) (Amersham, Pharmacia, Biotech).

Viral Neutralisation Assays:

The neutralising antibody titres for viruses IND, C486, B223, Wa and H2 in llama serum samples and purified VHH were determined by fluorescent focus neutralisation (FFN), as described in To, T. L. et al. (J Gen Virol 79 (Pt 11):2661-72, 1998). Briefly, 100 µl of serial dilutions of llama serum, selected purified VHH monomers or dimers were mixed with equal virus volumes in order to obtain 100 focus-forming units (FFU)/100 µl of mixture, and incubated for one hour at 37° C. 100 µl of the antibody-virus mixture were plated in MA-104 monolayers (4 replicates) and incubated for 48 hours at 37° C. The plates were fixed with 70% acetone and the assay was developed using an FITC-labelled anti-RV antibody from a colostrum-deprived calf hyperimmunised with RV. The VN titre was expressed as the reciprocal of the highest dilution in the sample that led to a >80% reduction in the number of fluorescent foci.

Example 4

Use of the Monomeric and Dimeric VHH of the Invention for the Prevention and/or Treatment of Mammals RV Protection Assays in Neonatal Mice:

100 µg of each anti-VP6 VHH monomer in 100 µl were administered to four-day-old Balb/c mice, using an intragastric probe, once a day, beginning on day 0, and for 5 days. The lactating mice were challenged with 100 µl of BRV C486 (SbI; P[1]G6), containing $2 \times 10^6$ FFU/ml, on day 1, 2 hours after the customary VHH dose, and then with 20 µl of a 5% bicarbonate solution, also by intragastric route. The innoculate was capable of producing diarrhoea in 100% of the untreated control mice. The control groups used in the experiment were: (i) mice innoculated with RV and not treated with antibodies; ii) mice treated with the same quantity of non-related VHH, directed against a cellular protein; iii) mice treated with 450 µg of affinity purified IgG derived from a guinea pig polyclonal antiserum with a VN titre of 2048 against the homologous RV; iv) mice treated with the same quantity of IgG from a seronegative control guinea pig; v) mice not infected and treated. The RV-induced diarrhoea was clinically evaluated by direct palpation of the mice's abdomen during the 5 days of the study. The severity of the diarrhoea was analysed on a daily basis, by assigning a numerical value based on the colour and consistency of the stools, as described by VanCott, J. L. et al., J Virol 80:4949-61, 2006.

Fisher's exact test was used to compare the proportions of mice with diarrhoea between the groups. The Kruskal Wallis non-parametric test was used to compare the mean onset, duration and severity of the diarrhoea between the treated groups.

Example 5

Recombinant Baculovirus Generation

Recombinant baculovirus BacMelVHH was generated from the phen 6 plasmid containing the VHH 3B2 complete sequence. The protein was PCR-amplified from the phen 6 plasmid using the following primers: SEQ ID NO: 23 and SEQ ID NO: 24. This amplicon was then cloned into the pFastMelB2 vector in frame with an insect signal sequence derived from the honey bee melitin, using the BamHI and XbaI restriction sites included at the corresponding primers. The resulting pFBMelVHH plasmid was characterized by automated sequencing and used to generate the recombinant baculovirus BacMelVHH using the Bac-to-Bac® Baculovirus system (Invitrogen, USA) following the manufacturer's instructions. Recombinant baculovirus was propagated and amplified in sf21 insect cells to reach infective titers between 107 and 109 pfu/ml and stocks were kept at 4° C. for daily use and –80° C. for long term storage.

Insect Growth Conditions and Inoculation

For expression experiments, fifth-instar larvae (last instar larvae before pupation) of about 250 mg weight, were injected with the recombinant baculoviruses near the proleg (forward the body cavity) using known pfu/larva doses. Infected larvae were kept in growth chambers at 28° C. and collected at indicated times. Larvae were then immediately frozen and kept at –20° C. until processed.

Insect cell cultures were also infected using known doses. Infected cells were kept at 28° C. for 72 h. Finally infected cultures were harvested and the cellular pellets were also immediately frozen and kept at –20° C. until processed.

Preparation of Protein Extracts

Total soluble proteins (TSP) from T. ni larvae were obtained by bending the freeze larvae in an extraction buffer containing triton 0.01%; DTT 25 mM and a protein inhibitor cocktail (Complete, Roche, Germany) in PBS 1×.

Analysis of Protein Extracts

A Coomassie blue staining and an immunoblotting analysis were performed for the quantification and detection of the specific VHH protein contained in the TSPS. Thus, 20 µg of TSP per lane were loaded in 12% SDS-polyacrylamide gels. After electrophoresis, gels were stained with a Coomassie blue solution or transferred to nitrocellulose membranes (Schleicher & Schuell,) to perform a western blot.

For Western blot assays SDS-PAGE (12%) was transferred onto nitrocellulose membrane (Bio-Rad, USA). Membrane was blocked overnight at 4° C. with PBS-0.05% Tween 20 (PBST) 4% skim milk (blocking buffer, BF) and then incubated at room temperature (RT) for 1 h using a rabbit anti-VHH serum (1:100 in BF). Membrane was washed 3 times with PBST and finally anti-rabbit IgG-HRP-labeled conjugated (1:2000 in BF, Sigma, USA) was added for 1 h as secondary antibody. After extensive washing with PBST, protein bands were detected using ECL Western blotting detection system on Hyperfilm ECL films (Amersham, USA) (See FIG. 6A).

Functional Analysis

TSP extracts from VP6 (a bovine rotavirus protein) expressing larvae [Ag(+)] or from infected larvae with a Non-insert recombinant baculovirus [Ag(–)] were used to coat ELISA microplates (Polysorp, Nunc, Denmark) with serial dilutions starting at 40 µg/well in 50 mM carbonate/bicarbonate buffer, pH 9.6 and incubated O.N at 4° C. Next day, plates were washed with PBST four times. Plates were sequentially incubated for 1 hour at 37° C. under constant agitation, with blocking solution (PBST-2% BSA, 100 µl/well) for 30 minutes. Then, with TSP extracts from VHH expressing larvae at 2.5 µg/well dilution in blocking buffer for 1 h. Plates were then washed 4 times with PBST and blocked again for 30 minutes. Then 100 µl/well of a polyclonal antibody (diluted 1:100) against the VHH made in rabbit was added and incubated for 1 h at 37° C. Plates were washed 4 times with PBST. Finally, 100 µl/well of anti-rabbit IgG-HRP labelled conjugated diluted 1:2000 in blocking solution was added. For substrate reaction, plates were washed four times and 100 µl/well of 1 mM 2,2"-Azino-bis(3-ethylbenzothiazoline-6-sulfonic acid) ABTS, (KPL, USA) were added to the plates. Peroxidase reaction was allowed to develop for 5-10 minutes at room temperature and reactions were read at 405 nm in an ELISA microplate reader (Multiskan EX, Thermo Electron Corp, USA) (See FIG. 7).

The invention claimed is:

1. A dimeric or monomeric VHH domain comprising SEQ ID NO: 4.

2. The domain according to claim 1, wherein the domain derives from antibodies of camelids selected from the group consisting of: *Lama glama, Lama pacos, Lama guanicoe* and *Vicugna vicugna*.

3. The domain according to claim 1, wherein the domain binds to a linear epitope of the VP6 antigen present in group A rotavirus.

4. A rotavirus immunodetection method, said method comprising: a) contacting a rotavirus-containing sample with an amino acid sequence comprising SEQ ID NO: 4; and b) detecting the rotavirus.

5. The method in accordance with claim 4, wherein said detecting is carried out using a technique selected from the group consisting of: immunocapture based tests ELISA, ELISPOT, competition ELISA, and magnetic beads.

6. A composition designed to confer passive immunity to a mammal, by the composition comprising: an amino acid sequence comprising SEQ ID NO: 4; excipients; and immunomodulators.

7. Plasmid pFBMeIVHH comprising a nucleotide sequence that encodes any of the monomeric or dimeric domains of claim 1.

8. A recombinant expression vector comprising the plasmid of claim 7.

9. The recombinant expression vector according to claim 8, wherein said vector is a viral vector.

10. An isolated transgenic cell transformed or transfected or infected with the vector of claim 8, wherein the cell expresses DNA included in plasmid pFBMeIVHH, wherein the plasmid pFBMeIVHH comprises a nucleotide sequence that encodes a monomeric or dimeric domain comprising SEQ ID NO: 4.

11. A method for the production of the domains of claim 1, said method comprising:
a) transforming or transfecting or infecting host cells in culture or in insect larvae with a recombinant expression vector, wherein said recombinant vector comprises a plasmid pFBMeIVHH that encodes the domain of claim 1;
b) keeping the cells growing under appropriate conditions; and
c) isolating and purifying the domains.

12. An antibody comprising any of the domains of claim 1.

13. A kit for immunodetection of rotavirus comprising an amino acid sequence comprising SEQ ID NO: 4.

14. An amino acid sequence comprising SEQ ID NO: 4, for use in a method for the treatment of infections produced by rotavirus.

15. A method for treating infections produced by Group A rotavirus, said method comprising administering an effective quantity of an amino acid sequence comprising SEQ ID NO: 4 to a mammal that needs it.

16. The method in accordance with claim 15, wherein administering comprises administering via a route selected from the group consisting of oral, intragastric, intravenous, and intraperitoneal routes.

17. The method in accordance with claim 15, wherein the mammal is selected from the group consisting of human beings, bovines, caprines, ovines, swines, and equines.

* * * * *

UNITED STATES PATENT AND TRADEMARK OFFICE
CERTIFICATE OF CORRECTION

PATENT NO. : 8,597,651 B2  
APPLICATION NO. : 12/670409  
DATED : December 3, 2013  
INVENTOR(S) : Surrey et al.

Page 1 of 1

It is certified that error appears in the above-identified patent and that said Letters Patent is hereby corrected as shown below:

In the Claims

Claim 6, Column 35, Line 37: change "mammal, by the composition comprising: an amino acid" to -- mammal, the composition comprising: an amino acid --

Signed and Sealed this  
Fourth Day of March, 2014

Michelle K. Lee  
*Deputy Director of the United States Patent and Trademark Office*